United States Patent [19]
Sager et al.

[11] Patent Number: 5,801,001
[45] Date of Patent: Sep. 1, 1998

[54] METHOD OF DETECTING CANCER

[75] Inventors: Ruth Sager, Brookline, Mass.; Zhiqiang Zou, Gaithersburg, Md.; Anthony Anisowicz, West Newton, Mass.

[73] Assignee: Dana-Farber Cancer Institute, Inc., Boston, Mass.

[21] Appl. No.: 477,108

[22] Filed: Jun. 7, 1995

Related U.S. Application Data

[60] Division of Ser. No. 121,714, Sep. 1, 1993, Pat. No. 5,470, 970, which is a continuation-in-part of Ser. No. 938,823, Sep. 1, 1992, abandoned, which is a continuation-in-part of Ser. No. 844,296, Feb. 28, 1992, abandoned, which is a continuation-in-part of Ser. No. 662,216, Feb. 28, 1991, abandoned.

[51] Int. Cl.$^6$ .................. G01N 33/536; G01N 33/574; C07K 16/30
[52] U.S. Cl. .................. 435/7.23; 435/7.21; 530/387.7; 530/387.9; 530/388.2; 530/388.8; 530/388.85; 530/389.7
[58] Field of Search .................. 435/7.1, 7.23; 530/387.7, 388.2, 387.9, 388.8, 388.85, 389.7

[56] References Cited

U.S. PATENT DOCUMENTS 4,888,278 12/1989 Singer et al.

OTHER PUBLICATIONS

Band and Sager, Distinctive Traits of Normal and Tumor-derived Human Mammary Epithelial Cells Expressed in a Medium that Supports Long-term . . . Growth of Both Cell Types, Proc. Natl. Acad. Sci. USA 86:1249–1253, 1989.
Band et al., Tumor Progression in Four Mammary Epithelial Cell Lines Derived from the Same Patient, Cancer Research, 50:7351–7357, 1990.
Band et al., A Newly Extablished Metastatic Breast Tumor Cell Line with Integrated Amplified Copies of ERBB2 and Double Minute Chromosomes, Genes, Chromosomes & Cancer 1:48–58, 1989.
Baumann et al., Crystal Structure of Cleaved Human $\alpha_1$–Antichymotrypsin at 2·7 Å Resolution and its Comparison with Other Serpins, J. Mol. Biol. 218:595–606, 1991.
Baylin et al., Hypermethylation of the 5' Region of the Calcitonin Gene is a Property of Human Lymphoid and Acute Myloid Malignancies, Blood 70:412–417,1987.
Calabretta et al., Molecular Cloning of the cDNA for a Growth Factor–inducible Gene with Strong Homology to S–100, a Calcium–binding Protein, J. Biol. Chem. 261:12628–12632, 1986.
Carr et al., The Tumorigenicity of 5–azacytidine in the Male Fischer Rat, Carcinogenesis 5:1583–1590, 1984.
Cattaneo et al., Altered Ratios of Measles Virus Transcripts in Diseased Human Brains, Virology 160:523–526, 1987.

Cowan et al., Similar Biochemical Changes Associated with Multidrug Resistance in Human Breast Cancer Cells and Carcinogen–induced Resistance to Xenobiotics in Rats, Proc. Natl. Acad. Sci. USA 83:9328–9332, 1986.
El–Deiry et al., High Expression of the DNA Methyltransferase Gene Characterizes Human Neoplastic Cells and Progression Stages of Colon Cancer, Proc. Natl. Acad. Sci. USA 88:3470–3474, 1991.
Friedmann, Gene Therapy, Therapy for Genetic Disease, pp. 107–121.
Gibbs et al., Characterization of the HUman spr2 Promoter: Induction after UV Irradiation or TPA Treatment and Regulation During Differentiation of . . . Primary Keratinocytes, Nucleic Acids Res. 18:4401–4407, 1990.
Harrison et al., Azacytidine–induced Tumorigenesis of CHEF/18 Cells: Correlated DNA Methylation and Chromosome Changes, Proc. Natl. Acad. Sci. USA 80: 6606–6610, 1983.
Hendrix et al., A Simple Quantitative Assay for Studying the Invasive Potential of High and Low Human Metastatic Varients, Cancer Letters 38:137–147, 1987.
Huber et al., Implications of the Three–Dimensional Structure of $\alpha_1$–Antitrypsin for Structure and Function of Serpins, Biochemistry 28:8951–8966, 1989.
Jones and Buckley, The Role of DNA Methylation in Cancer, Advances in Cancer Research 54:1–23, 1990.
Kligman and Hilt, The s100 Protein Family, Trends in Biochemical Sciences 13:437–443, 1988.
Lee et al., Down–regulation of a Member of the s100 Gene Family in Mammary Carcinoma Cells and Reexpression by Azadeoxycytidine Treatment, Proc. Natl. Acad. Sci. UsA 89:2504–2508, 1992.
Lee et al., Positive Selection of Candidate Tumor–Suppressor Genes by Subtractive Hybridization, Proc. Natl. Acad. Sci. USA 88:2825–2829, 1991.
Lee et al., Isolation and Characterization of Eight Tumor Necrosis Factor–Induced Gene Sequences from Human Fibroblasts, Molecular and Cellular Biology 10:1982–1988, 1990.
Lersch and Fuchs, Sequence and Expression of a Type II Keratin, K5, in Human Epidermal Cells, Molecular and Cellular Biology 8:486–493, 1988.
Liotta and Stetler–Stevenson, Tumor Invasion and Metastasis: An Imbalance of Positive and Negative Regulation, Cancer Research(Suppl.) 51:5054s–5059s, 1991.
Lobermann et al., Human $\alpha_a$–Proteinase Inhibitor, J. Mol. Biol. 177:531–556, 1984.

(List continued on next page.)

Primary Examiner—Lila Feisee
Assistant Examiner—Nancy Johnson
Attorney, Agent, or Firm—Fish & Richardson P.C.

[57] ABSTRACT

An isolated DNA encoding a polypeptide substantially identical to maspin (SEQ ID NO:1); a substantially purified preparation of maspin; an antibody specific for maspin; and use of such DNAs and antibodies in diagnostic, screening, and therapeutic methods.

27 Claims, 9 Drawing Sheets

OTHER PUBLICATIONS

Moscow et al., Expression of Anionic Glutathione–S–transferase and P–Glycoprotein Genes in Human Tissues and Tumors, Cancer Research 49:1422–1428, 1989.

Mottonen et al., Structural basis of Latency in Plasminogen Activator Inhibitor–1, Nature 355:270–273, 1992.

Price et al., Tumorigenicity and Metastasis of Human Breast Carcinoma Cell lines in Nude Mice, Cancer Research 50:717–721, 1990.

PCT Search Report in the corresponding PCT Application No. PCT/US93/08322, mailed Nov. 2, 1993.

Remond–O'Donnell et al., Sequence and Molecular Characterization of Human Monocyte/Neutrophil Elastase Inhibitor, Proc. Natl. Acad. Sci. USA 89:5635–5639, 1992.

Sager et al., Identification by Differential Display of Alpha 6 Integrin as a Candidate Tumor Suppressor Gene, FASEB J. 7:964–970, 1993.

Sager, Tumor Suppressor Genes: The Puzzle and the Promise, Science 246:1406–1412, 1989.

Saheki et al., Primary Structure of the Human Elafin Presursor Preproelafin Deduced from the Nucleotide Sequence . . . . Repetitive Sequences in the Prosegment, Biochem. & Biophys. Research Comm. 185:240–245, 1992.

Stein et al., Crystal Structure of Ovalbumin as a Model for the Reactive Centre of Serpins, Nature 347:99–102, 1990.

Testa and Quigley, The Role of Urokinase–type Plasminogen Activator in Aggressive Tumor Cell Behavior, Cancer and Metastasis Reviews 9:353–367, 1990.

Tomasetto et al., Specificity of Gap Junction Communication Among Human Mammary Cells and Connexin Transfectants in Culture, J. Cell Biol. 122:157–167, 1993.

Trask et al., Keratins as Markers that Distinguish Normal and Tumor–derived Mammary Epithelial Cells, Proc. Natl. Acad. Sci. USA 87:2319–2323, 1990.

Travis et al., Serpins: Structure and Mechanism of Action, Biological Chemistry Hoppe–Seyler 371(Suppl.): 3–11, 1990.

Tsunemi et al., Synthesis and Structure–Activity Relationships of Elafin, an Elastase–Specific Inhibitor, Biochemical and Biophysical Research Communications 185:967–973, 1992.

Wiedow et al., Elafin: An Elastase–specific Inhibitor of Human Skin, J. Biol. Chem. 265:14791–14795, 1990.

Wright et al., Crystal Structure of Plakalbumin, a Proteolytically Nicked Form of Ovalbumin, J. Mol. Biol. 213:513–528, 1990.

Yaswen et al., Down–regulation of a Calmodulin–related Gene During Transformation of Human Mammary Epithelial Cells, Proc. Natl. Acad. Sci. USA 87:7360–7364, 1990.

Zhang and Nicholson, Sequence and Tissue Distribution of a Second Protein of Hepatic Gap Junctions, Cx26, As Deduced from its cDNA, J. Cell Biol. 109:3391–3401, 1989.

Webb et al., Human Monocyte Arg–Serpin cDNA Sequence, Chromosomal Assignment, and Homology to Plasminogen Activator–Inhibitor, J. Exp. Med. 166:77–94, 1987.

Zou et al., Maspin, a Serpin with Tumor–Suppressing Activity in Human Mammary Epithelial Cells, Science 263:526–529, 1994.

Sager, Genetic Suppression of Tumor Formation: A New Frontier in Cancer Research, Cancer Research 46:1573–1580, 1986.

Sager, Genetic Suppression of Tumor Formation, Advances in Cancer Research 44:43–68, 1985.

Schweinfest et al., Subtraction Hybridization cDNA Libraries from Colon Carcinoma and Hepatic Cancer, Genet Annal Techn. Appl 7:64–70, 1990.

Swaroop et al., A Simple and Efficient cDNA Library Subtraction Procedure: Isolation of Human Retina–Specific cDNA Clones, Nucleic Acids Research 19:1954, 1991.

```
GGCACGAGTT GTGCTCCTCG CTTGCCTGTT CCTTTTCCAC GCATTTTCCA GGATAACTGT    60

GACTCCAGGC CCGCA ATG GAT GCC CTG CAA CTA GCA AAT TCG GCT TTT GCC   111
                Met Asp Ala Leu Gln Leu Ala Asn Ser Ala Phe Ala

GTT GAT TTG TTC AAA CAA CTA TGT GAA AAG GAG CCA CTG GGC AAT GTC   159
Val Asp Leu Phe Lys Gln Leu Cys Glu Lys Glu Pro Leu Gly Asn Val

CTC TTC TCT CCA ATC TGT CTC TCC ACC TCT CTG TCA CTT GCT CAA GTG   207
Leu Phe Ser Pro Ile Cys Leu Ser Thr Ser Leu Ser Leu Ala Gln Val

GGT GCT AAA GGT GAC ACT GCA AAT GAA ATT GGA CAG GTT CTT CAT TTT   255
Gly Ala Lys Gly Asp Thr Ala Asn Glu Ile Gly Gln Val Leu His Phe

GAA AAT GTC AAA GAT ATA CCC TTT GGA TTT CAA ACA GTA ACA TCG GAT   303
Glu Asn Val Lys Asp Ile Pro Phe Gly Phe Gln Thr Val Thr Ser Asp

GTA AAC AAA CTT AGT TCC TTT TAC TCA CTG AAA CTA ATC AAG CGG CTC   351
Val Asn Lys Leu Ser Ser Phe Tyr Ser Leu Lys Leu Ile Lys Arg Leu

TAC GTA GAC AAA TCT CTG AAT CTT TCT ACA GAG TTC ATC AGC TCT ACG   399
Tyr Val Asp Lys Ser Leu Asn Leu Ser Thr Glu Phe Ile Ser Ser Thr

AAG AGA CCC TAT GCA AAG GAA TTG GAA ACT GTT GAC TTC AAA GAT AAA   447
Lys Arg Pro Tyr Ala Lys Glu Leu Glu Thr Val Asp Phe Lys Asp Lys

TTG GAA GAA ACG AAA GGT CAG ATC AAC AAC TCA ATT AAG GAT CTC ACA   495
Leu Glu Glu Thr Lys Gly Gln Ile Asn Asn Ser Ile Lys Asp Leu Thr

GAT GGC CAC TTT GAG AAC ATT TTA GCT GAC AAC AGT GTG AAC GAC CAG   543
Asp Gly His Phe Glu Asn Ile Leu Ala Asp Asn Ser Val Asn Asp Gln

ACC AAA ATC CTT GTG GTT AAT GCT GCC TAC TTT GTT GGC AAG TGG ATG   591
Thr Lys Ile Leu Val Val Asn Ala Ala Tyr Phe Val Gly Lys Trp Met

AAG AAA TTT CCT GAA TCA GAA ACA AAA GAA TGT CCT TTC AGA CTC AAC   639
Lys Lys Phe Pro Glu Ser Glu Thr Lys Glu Cys Pro Phe Arg Leu Asn

AAG ACA GAC ACC AAA CCA GTG CAG ATG ATG AAC ATG GAG GCC ACG TTC   687
Lys Thr Asp Thr Lys Pro Val Gln Met Met Asn Met Glu Ala Thr Phe
```

FIG. 3-1

```
TGT ATG GGA AAC ATT GAC AGT ATC AAT TGT AAG ATC ATA GAG CTT CCT    735
Cys Met Gly Asn Ile Asp Ser Ile Asn Cys Lys Ile Ile Glu Leu Pro

TTT CAA AAT AAG CAT CTC AGC ATG TTC ATC CTA CTA CCC AAG GAT GTG    783
Phe Gln Asn Lys His Leu Ser Met Phe Ile Leu Leu Pro Lys Asp Val

GAG GAT GAG TCC ACA GGC TTG GAG AAG ATT GAA AAA CAA CTC AAC TCA    831
Glu Asp Glu Ser Thr Gly Leu Glu Lys Ile Glu Lys Gln Leu Asn Ser

GAG TCA CTG TCA CAG TGG ACT AAT CCC AGC ACC ATG GCC AAT GCC AAG    879
Glu Ser Leu Ser Gln Trp Thr Asn Pro Ser Thr Met Ala Asn Ala Lys

GTC AAA CTC TCC ATT CCA AAA TTT AAG GTG GAA AAG ATG ATT GAT CCC    927
Val Lys Leu Ser Ile Pro Lys Phe Lys Val Glu Lys Met Ile Asp Pro

AAG GCT TGT CTG GAA AAT CTA GGG CTG AAA CAT ATC TTC AGT GAA GAC    975
Lys Ala Cys Leu Glu Asn Leu Gly Leu Lys His Ile Phe Ser Glu Asp

ACA TCT GAT TTC TCT GGA ATG TCA GAG ACC AAG GGA GTG GCC CTA TCA   1023
Thr Ser Asp Phe Ser Gly Met Ser Glu Thr Lys Gly Val Ala Leu Ser

AAT GTT ATC CAC AAA GTG TGC TTA GAA ATA ACT GAA GAT GGT GGG GAT   1071
Asn Val Ile His Lys Val Cys Leu Glu Ile Thr Glu Asp Gly Gly Asp

TCC ATA GAG GTG CCA GGA GCA CGG ATC CTG CAG CAC AAG GAT GAA TTG   1119
Ser Ile Glu Val Pro Gly Ala Arg Ile Leu Gln His Lys Asp Glu Leu

AAT GCT GAC CAT CCC TTT ATT TAC ATC ATC AGG CAC AAC AAA ACT CGA   1167
Asn Ala Asp His Pro Phe Ile Tyr Ile Ile Arg His Asn Lys Thr Arg

AAC ATC ATT TTC TTT GGC AAA TTC TGT TCT CCT TAAGTGGCAT AGCCCATGTT 1220
Asn Ile Ile Phe Phe Gly Lys Phe Cys Ser Pro

AAGTCCTCCC TGACTTTTCT GTGGATGCCG ATTTCTGTAA ACTCTGCATC CAGAGATTCA 1280
TTTTCTAGAT ACAATAAATT GCTAATGTTG CTGGATCAGG AAGCCGCCAG TACTTGTCAT 1340
ATGTAGCCTT CACACAGATA GACCTTTTTT TTTTTCCAAT TCTATCTTTT GTTTCCTTTT 1400
TTCCCATAAG ACAATGACAT ACGCTTTTAA TGAAAAGGAA TCACGTTAGA GGAAAAATAT 1460
TTATTCATTA TTTGTCAAAT TGTCCGGGGT AGTTGGCAGA AATACAGTCT TCCACAAAGA 1520
```

FIG. 3-2

```
AAATTCCTAT AAGGAAGATT TGGAAGCTCT TCTTCCCAGC ACTATGCTTT CCTTCTTTGG 1580
GATAGAGAAT GTTCCAGACA TTCTCGCTTC CCTGAAAGAC TGAAGAAAGT GTAGTGCATG 1640
GGACCCACGA AACTGCCCTG GCTCCAGTGA AACTTGGGCA CATGCTCAGG CTACTATAGG 1700
TCCAGAAGTC CTTATGTTAA GCCCTGGCAG GCAGGTGTTT ATTAAAATTC TGAATTTTGG 1760
GGATTTTCAA AAGATAATAT TTTACATACA CTGTATGTTA TAGAACTTCA TGGATCAGAT 1820
CTGGGGCAGC AACCTATAAA TCAACACCTT AATATGCTGC AACAAAATGT AGAATATTCA 1880
GACAAAATGG ATACATAAAG ACTAAGTAGC CCATAAGGGG TCAAAATTTG CTGCCAAATG 1940
CGTATGCCAC CAACTTACAA AAACACTTCG TTCGCAGAGC TTTTCAGATT GTGGAATGTT 2000
GGATAAGGAA TTATAGACCT CTAGTAGCTG AAATGCAAGA CCCCAAGAGG AAGTTCAGAT 2060
CTTAATATAA ATTCACTTTC ATTTTTGATA GCTGTCCCAT CTGGTCATGT GGTTGGCACT 2120
AGACTGGTGG CAGGGGCTTC TAGCTGACTC GCACAGGGAT TCTCACAATA GCCGATATCA 2180
GAATTTGTGT TGAAGGAACT TGTCTCTTCA TCTAATATGA TAGCGGGAAA AGGAGAGGAA 2240
ACTACTGCCT TTAGAAAATA TAAGTAAAGT GATTAAAGTG CTCACGTTAC CTTGACACAT 2300
AGTTTTTCAG TCTATGGGTT TAGTTACTTT AGATGGCAAG CATGTAACTT ATATTAATAG 2360
TAATTTGTAA AGTTGGGTGG ATAAGCTATC CCTGTTGCCG GTTCATGGAT TACTTCTCTA 2420
TAAAAAATAT ATATTTACCA AAAAATTTTG TGACATTCCT TCTCCCATCT CTTCCTTGAC 2480
ATGCATTGTA AATAGGTTCT TCTTGTTCTG AGATTCAATA TTGAATTTCT CCTATGCTAT 2540
TGACAATAAA ATATTATTGA ACTACCAAAA AAAAAAAAA AAAA          2584
```

```
serapin   DIEDESTGLE KIEKQLTLEK LREWTKPENL YLAEVNVHLP RFKLEESYDL TSHLARLGVQ DLFNRGKADL SGMSGARDLF
ei        DIEDESTGIK KIEEQLTLEK LHEWTKPENL DFIEVNVSLP RFKLEESVTL NSDLARLGVQ DLFNSSKADL SGMSGARDIF
maspin    DVEDESTGLE KIEKQLNSES ISQWTNPSTM ANAKVKLSIP KFKKVEKMIDP KACLENLGLK HIFSEDTSDF SGMSETKGVA
pai2      EIADVSTGLE ILESEITYDK LNKWISKDKM AEDEVEVYIP QFKLEEHYEL RGILRSMGME DAFNKGRANF SGMSERNDLF
pail      EKF...VPLS ALTNILSAQL ISHWK..GNM TRLPRLLVLP KFSLETEVDL RKPLENLGMT DMFRQFQADF TSLSDQEPLH
at        PDE....GKLQ HLENELTHDI ITKFL..ENE DRRSASLHLP KFSILETEVDL KSVLGQLGIT KVFSN.GADL SGVTEEAPLK
ovalbu    EV....SGLE QLESIINFEK ITEWTSSNVM EERKMEEKYNL TSVLMAMGIT DVFSS..ANL SGISSAESLK 401                                                                         468
serapin   VSKTIHKSFV DLNEEGTEAA AATAGTIMLA MLMPEENFNA DHPFLFFIRH NPSANILFLG RFSSPX...
ei        ISKIVHKSFV EVNEEGTEAA AATAGIATFC MLMPEENFTA DHPFLFFIRH NSSGSILFLG RFSSPX...
maspin    ISNVIHKVCL EIEDGGDSI  EVPGA....R ILQHKDELNA DHPFIYIRH  NKTRNIFFG  KFCSPX...
pai2      LSEVFHQAMV DVNEEGTEAA AGTGGVMTGR TGHGGPQFVA DHPFLFLIMH DRPFLFVRH  KITKCILFFG RFCSP...
pail      VAQALQKVKI EVNESGTVAS SSTAVIVSAR MA..PEEIIM NKPFVFLMIE QNIKSPLFMG QVMEP...
at        ISKAVHKAVL TIDEKGTEAA GAMFLEAIPM SI..PPEVKF SEEFRA     DHPFLFCIMH IAINAVLFFG KVVNPTQK...
ovalbu    ISQAVHAAHA EINEAGREVV GSAEAGVDAA SV..SEEFRA           DHPFLFCIMH IAINAVLFFG RCVEP...
                                          AbS3A
```

FIG. 4-2

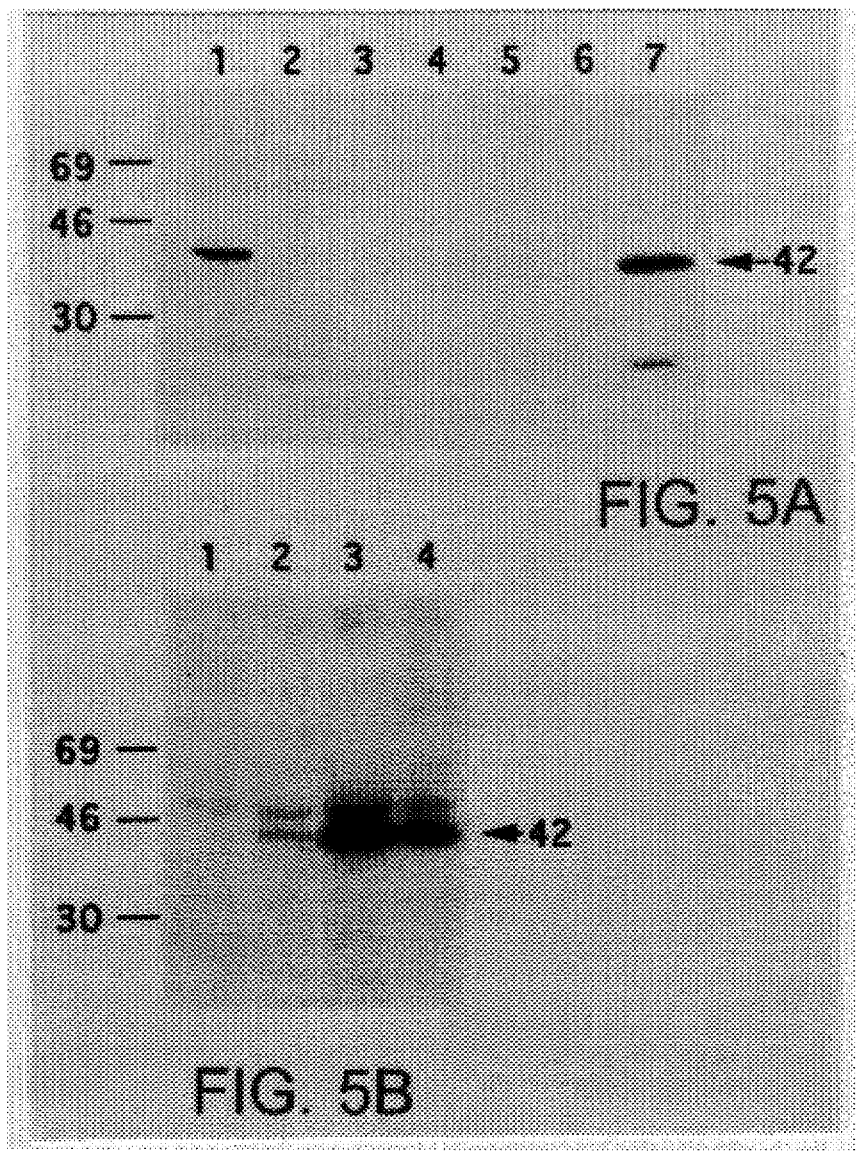

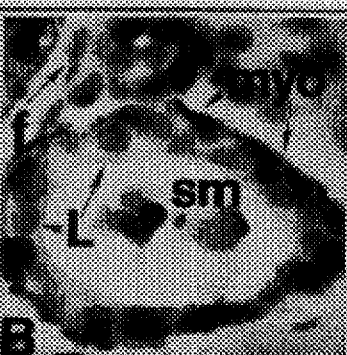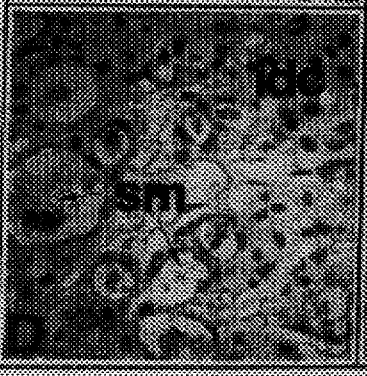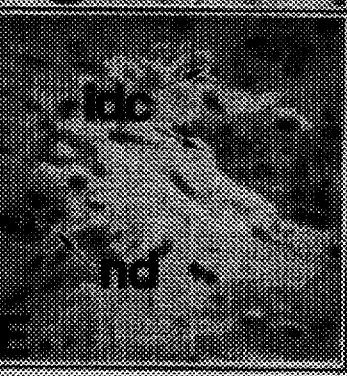
FIG. 6A  FIG. 6B  FIG. 6C  FIG. 6D  FIG. 6E  FIG. 6F
FIG. 7

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
  ( A ) LENGTH: 2584
  ( B ) TYPE: nucleic acid
  ( C ) STRANDEDNESS: double
  ( D ) TOPOLOGY: linear ( x i ) SEQUENCE DESCRIPTION: SEQ ID NO: 1:

```
GGCACGAGTT  GTGCTCCTCG  CTTGCCTGTT  CCTTTTCCAC  GCATTTTCCA  GGATAACTGT          60

GACTCCAGGC  CCGCA ATG GAT GCC CTG CAA CTA GCA AAT TCG GCT TTT GCC              111
                 Met Asp Ala Leu Gln Leu Ala Asn Ser Ala Phe Ala
                  1               5                  10

GTT GAT CTG TTC AAA CAA CTA TGT GAA AAG GAG CCA CTG GGC AAT GTC                159
Val Asp Leu Phe Lys Gln Leu Cys Glu Lys Glu Pro Leu Gly Asn Val
         15                  20                  25

CTC TTC TCT CCA ATC TGT CTC TCC ACC TCT CTG TCA CTT GCT CAA GTG                207
Leu Phe Ser Pro Ile Cys Leu Ser Thr Ser Leu Ser Leu Ala Gln Val
     30                  35                  40

GGT GCT AAA GGT GAC ACT GCA AAT GAA ATT GGA CAG GTT CTT CAT TTT                255
Gly Ala Lys Gly Asp Thr Ala Asn Glu Ile Gly Gln Val Leu His Phe
 45                  50                  55                  60

GAA AAT GTC AAA GAT ATA CCC TTT GGA TTT CAA ACA GTA ACA TCG GAT                303
Glu Asn Val Lys Asp Ile Pro Phe Gly Phe Gln Thr Val Thr Ser Asp
                 65                  70                  75

GTA AAC AAA CTT AGT TCC TTT TAC TCA CTG AAA CTA ATC AAG CGG CTC                351
Val Asn Lys Leu Ser Ser Phe Tyr Ser Leu Lys Leu Ile Lys Arg Leu
             80                  85                  90

TAC GTA GAC AAA TCT CTG AAT CTT TCT ACA GAG TTC ATC AGC TCT ACG                399
Tyr Val Asp Lys Ser Leu Asn Leu Ser Thr Glu Phe Ile Ser Ser Thr
         95                 100                 105

AAG AGA CCC TAT GCA AAG GAA TTG GAA ACT GTT GAC TTC AAA GAT AAA                447
Lys Arg Pro Tyr Ala Lys Glu Leu Glu Thr Val Asp Phe Lys Asp Lys
    110                 115                 120

TTG GAA GAA ACG AAA GGT CAG ATC AAC AAC TCA ATT AAG GAT CTC ACA                495
Leu Glu Glu Thr Lys Gly Gln Ile Asn Asn Ser Ile Lys Asp Leu Thr
125                 130                 135                 140

GAT GGC CAC TTT GAG AAC ATT TTA GCT GAC AAC AGT GTG AAC GAC CAG                543
Asp Gly His Phe Glu Asn Ile Leu Ala Asp Asn Ser Val Asn Asp Gln
                145                 150                 155

ACC AAA ATC CTT GTG GTT AAT GCT GCC TAC TTT GTT GGC AAG TGG ATG                591
Thr Lys Ile Leu Val Val Asn Ala Ala Tyr Phe Val Gly Lys Trp Met
            160                 165                 170
```

-continued

| | | | | | | | | | | | | | | | | |
|---|---|---|---|---|---|---|---|---|---|---|---|---|---|---|---|---|
| AAG | AAA | TTT | CCT | GAA | TCA | GAA | ACA | AAA | GAA | TGT | CCT | TTC | AGA | CTC | AAC | 639 |
| Lys | Lys | Phe | Pro | Glu | Ser | Glu | Thr | Lys | Glu | Cys | Pro | Phe | Arg | Leu | Asn | |
| | | 175 | | | | | 180 | | | | | 185 | | | | |
| AAG | ACA | GAC | ACC | AAA | CCA | GTG | CAG | ATG | ATG | AAC | ATG | GAG | GCC | ACG | TTC | 687 |
| Lys | Thr | Asp | Thr | Lys | Pro | Val | Gln | Met | Met | Asn | Met | Glu | Ala | Thr | Phe | |
| | | | 190 | | | | 195 | | | | | 200 | | | | |
| TGT | ATG | GGA | AAC | ATT | GAC | AGT | ATC | AAT | TGT | AAG | ATC | ATA | GAG | CTT | CCT | 735 |
| Cys | Met | Gly | Asn | Ile | Asp | Ser | Ile | Asn | Cys | Lys | Ile | Ile | Glu | Leu | Pro | |
| 205 | | | | | 210 | | | | | 215 | | | | | 220 | |
| TTT | CAA | AAT | AAG | CAT | CTC | AGC | ATG | TTC | ATC | CTA | CTA | CCC | AAG | GAT | GTG | 783 |
| Phe | Gln | Asn | Lys | His | Leu | Ser | Met | Phe | Ile | Leu | Leu | Pro | Lys | Asp | Val | |
| | | | | 225 | | | | | 230 | | | | | 235 | | |
| GAG | GAT | GAG | TCC | ACA | GGC | TTG | GAG | AAG | ATT | GAA | AAA | CAA | CTC | AAC | TCA | 831 |
| Glu | Asp | Glu | Ser | Thr | Gly | Leu | Glu | Lys | Ile | Glu | Lys | Gln | Leu | Asn | Ser | |
| | | | | 240 | | | | | 245 | | | | | 250 | | |
| GAG | TCA | CTG | TCA | CAG | TGG | ACT | AAT | CCC | AGC | ACC | ATG | GCC | AAT | GCC | AAG | 879 |
| Glu | Ser | Leu | Ser | Gln | Trp | Thr | Asn | Pro | Ser | Thr | Met | Ala | Asn | Ala | Lys | |
| | | | 255 | | | | | 260 | | | | | 265 | | | |
| GTC | AAA | CTC | TCC | ATT | CCA | AAA | TTT | AAG | GTG | GAA | AAG | ATG | ATT | GAT | CCC | 927 |
| Val | Lys | Leu | Ser | Ile | Pro | Lys | Phe | Lys | Val | Glu | Lys | Met | Ile | Asp | Pro | |
| | 270 | | | | | 275 | | | | | 280 | | | | | |
| AAG | GCT | TGT | CTG | GAA | AAT | CTA | GGG | CTG | AAA | CAT | ATC | TTC | AGT | GAA | GAC | 975 |
| Lys | Ala | Cys | Leu | Glu | Asn | Leu | Gly | Leu | Lys | His | Ile | Phe | Ser | Glu | Asp | |
| 285 | | | | | 290 | | | | | 295 | | | | | 300 | |
| ACA | TCT | GAT | TTC | TCT | GGA | ATG | TCA | GAG | ACC | AAG | GGA | GTG | GCC | CTA | TCA | 1023 |
| Thr | Ser | Asp | Phe | Ser | Gly | Met | Ser | Glu | Thr | Lys | Gly | Val | Ala | Leu | Ser | |
| | | | | 305 | | | | | 310 | | | | | 315 | | |
| AAT | GTT | ATC | CAC | AAA | GTG | TGC | TTA | GAA | ATA | ACT | GAA | GAT | GGT | GGG | GAT | 1071 |
| Asn | Val | Ile | His | Lys | Val | Cys | Leu | Glu | Ile | Thr | Glu | Asp | Gly | Gly | Asp | |
| | | | | 320 | | | | | 325 | | | | | 330 | | |
| TCC | ATA | GAG | GTG | CCA | GGA | GCA | CGG | ATC | CTG | CAG | CAC | AAG | GAT | GAA | TTG | 1119 |
| Ser | Ile | Glu | Val | Pro | Gly | Ala | Arg | Ile | Leu | Gln | His | Lys | Asp | Glu | Leu | |
| | | 335 | | | | | 340 | | | | | 345 | | | | |
| AAT | GCT | GAC | CAT | CCC | TTT | ATT | TAC | ATC | ATC | AGG | CAC | AAC | AAA | ACT | CGA | 1167 |
| Asn | Ala | Asp | His | Pro | Phe | Ile | Tyr | Ile | Ile | Arg | His | Asn | Lys | Thr | Arg | |
| | 350 | | | | | 355 | | | | | 360 | | | | | |
| AAC | ATC | ATT | TTC | TTT | GGC | AAA | TTC | TGT | TCT | CCT | TAAGTGGCAT | | | AGCCCATGTT | | 1220 |
| Asn | Ile | Ile | Phe | Phe | Gly | Lys | Phe | Cys | Ser | Pro | | | | | | |
| 365 | | | | | 370 | | | | | 375 | | | | | | |

AAGTCCTCCC TGACTTTTCT GTGGATGCCG ATTTCTGTAA ACTCTGCATC CAGAGATTCA 1280
TTTTCTAGAT ACAATAAATT GCTAATGTTG CTGGATCAGG AAGCCGCCAG TACTTGTCAT 1340
ATGTAGCCTT CACACAGATA GACCTTTTTT TTTTTCCAAT TCTATCTTTT GTTTCCTTTT 1400
TTCCATAAG ACAATGACAT ACGCTTTAA TGAAAAGGAA TCACGTTAGA GGAAAAATAT 1460
TTATTCATTA TTTGTCAAAT TGTCCGGGGT AGTTGGCAGA AATACAGTCT TCCACAAAGA 1520
AAATTCCTAT AAGGAAGATT TGGAAGCTCT TCTTCCCAGC ACTATGCTTT CCTTCTTTGG 1580
GATAGAGAAT GTTCCAGACA TTCTCGCTTC CCTGAAAGAC TGAAGAAAGT GTAGTGCATG 1640
GGACCCACGA AACTGCCCTG GCTCCAGTGA ACTTGGGCA CATGCTCAGG CTACTATAGG 1700
TCCAGAAGTC CTTATGTTAA GCCCTGGCAG GCAGGTGTTT ATTAAAATTC TGAATTTTGG 1760
GGATTTTCAA AAGATAATAT TTTACATACA CTGTATGTTA TAGAACTTCA TGGATCAGAT 1820
CTGGGGCAGC AACCTATAAA TCAACACCTT AATATGCTGC AACAAAATGT AGAATATTCA 1880
GACAAAATGG ATACATAAAG ACTAAGTAGC CCATAAGGGG TCAAAATTTG CTGCCAAATG 1940
CGTATGCCAC CAACTTACAA AAACACTTCG TTCGCAGAGC TTTTCAGATT GTGGAATGTT 2000
GGATAAGGAA TTATAGACCT CTAGTAGCTG AAATGCAAGA CCCCAAGAGG AAGTTCAGAT 2060

```
CTTAATATAA ATTCACTTTC ATTTTTGATA GCTGTCCCAT CTGGTCATGT GGTTGGCACT      2120

AGACTGGTGG CAGGGGCTTC TAGCTGACTC GCACAGGGAT TCTCACAATA GCCGATATCA      2180

GAATTTGTGT TGAAGGAACT TGTCTCTTCA TCTAATATGA TAGCGGGAAA AGGAGAGGAA      2240

ACTACTGCCT TTAGAAAATA TAAGTAAAGT GATTAAAGTG CTCACGTTAC CTTGACACAT      2300

AGTTTTTCAG TCTATGGGTT TAGTTACTTT AGATGGCAAG CATGTAACTT ATATTAATAG      2360

TAATTTGTAA AGTTGGGTGG ATAAGCTATC CCTGTTGCCG GTTCATGGAT TACTTCTCTA      2420

TAAAAAATAT ATATTTACCA AAAAATTTTG TGACATTCCT TCTCCCATCT CTTCCTTGAC      2480

ATGCATTGTA AATAGGTTCT TCTTGTTCTG AGATTCAATA TTGAATTTCT CCTATGCTAT      2540

TGACAATAAA ATATTATTGA ACTACCAAAA AAAAAAAAA AAAA                        2584
```

( 2 ) INFORMATION FOR SEQ ID NO: 2:

( i ) SEQUENCE CHARACTERISTICS:
( A ) LENGTH:375
( B ) TYPE: amino acid
( C ) STRANDEDNESS:
( D ) TOPOLOGY: linear ( x i ) SEQUENCE DESCRIPTION: SEQ ID NO: 2:

```
Met Asp Ala Leu Gln Leu Ala Asn Ser Ala Phe Ala Val Asp Leu Phe
 1               5                  10                  15

Lys Gln Leu Cys Glu Lys Glu Pro Leu Gly Asn Val Leu Phe Ser Pro
                20                  25                  30

Ile Cys Leu Ser Thr Ser Leu Ser Leu Ala Gln Val Gly Ala Lys Gly
            35                  40                  45

Asp Thr Ala Asn Glu Ile Gly Gln Val Leu His Phe Glu Asn Val Lys
    50                  55                  60

Asp Ile Pro Phe Gly Phe Gln Thr Val Thr Ser Asp Val Asn Lys Leu
65                  70                  75                  80

Ser Ser Phe Tyr Ser Leu Lys Leu Ile Lys Arg Leu Tyr Val Asp Lys
                85                  90                  95

Ser Leu Asn Leu Ser Thr Glu Phe Ile Ser Ser Thr Lys Arg Pro Tyr
            100                 105                 110

Ala Lys Glu Leu Glu Thr Val Asp Phe Lys Asp Lys Leu Glu Glu Thr
        115                 120                 125

Lys Gly Gln Ile Asn Asn Ser Ile Lys Asp Leu Thr Asp Gly His Phe
    130                 135                 140

Glu Asn Ile Leu Ala Asp Asn Ser Val Asn Asp Gln Thr Lys Ile Leu
145                 150                 155                 160

Val Val Asn Ala Ala Tyr Phe Val Gly Lys Trp Met Lys Lys Phe Pro
                165                 170                 175

Glu Ser Glu Thr Lys Glu Cys Pro Phe Arg Leu Asn Lys Thr Asp Thr
            180                 185                 190

Lys Pro Val Gln Met Met Asn Met Glu Ala Thr Phe Cys Met Gly Asn
        195                 200                 205

Ile Asp Ser Ile Asn Cys Lys Ile Ile Glu Leu Pro Phe Gln Asn Lys
    210                 215                 220

His Leu Ser Met Phe Ile Leu Leu Pro Lys Asp Val Glu Asp Glu Ser
225                 230                 235                 240

Thr Gly Leu Glu Lys Ile Glu Lys Gln Leu Asn Ser Glu Ser Leu Ser
                245                 250                 255

Gln Trp Thr Asn Pro Ser Thr Met Ala Asn Ala Lys Val Lys Leu Ser
            260                 265                 270
```

```
Ile  Pro  Lys  Phe  Lys  Val  Glu  Lys  Met  Ile  Asp  Pro  Lys  Ala  Cys  Leu
          275                      280                     285

Glu  Asn  Leu  Gly  Leu  Lys  His  Ile  Phe  Ser  Glu  Asp  Thr  Ser  Asp  Phe
          290                      295                     300

Ser  Gly  Met  Ser  Glu  Thr  Lys  Gly  Val  Ala  Leu  Ser  Asn  Val  Ile  His
305                      310                     315                      320

Lys  Val  Cys  Leu  Glu  Ile  Thr  Glu  Asp  Gly  Gly  Asp  Ser  Ile  Glu  Val
                    325                      330                     335

Pro  Gly  Ala  Arg  Ile  Leu  Gln  His  Lys  Asp  Glu  Leu  Asn  Ala  Asp  His
               340                      345                     350

Pro  Phe  Ile  Tyr  Ile  Ile  Arg  His  Asn  Lys  Thr  Arg  Asn  Ile  Ile  Phe
          355                      360                     365

Phe  Gly  Lys  Phe  Cys  Ser  Pro
          370                 375
```

( 2 ) INFORMATION FOR SEQ ID NO: 3:

( i ) SEQUENCE CHARACTERISTICS:
        ( A ) LENGTH:418
        ( B ) TYPE: amino acid
        ( C ) STRANDEDNESS:
        ( D ) TOPOLOGY: linear ( x i ) SEQUENCE DESCRIPTION: SEQ ID NO: 3:

```
Met  Pro  Ser  Ser  Val  Ser  Trp  Gly  Ile  Leu  Leu  Leu  Ala  Gly  Leu  Cys
 1              5                        10                      15

Cys  Leu  Val  Pro  Val  Ser  Leu  Ala  Glu  Asp  Pro  Gln  Gly  Asp  Ala  Ala
               20                      25                      30

Gln  Lys  Thr  Asp  Thr  Ser  His  His  Asp  Gln  Asp  His  Pro  Thr  Phe  Asn
          35                      40                      45

Lys  Ile  Thr  Pro  Asn  Leu  Ala  Glu  Phe  Ala  Phe  Ser  Leu  Tyr  Arg  Gln
 50                      55                      60

Leu  Ala  His  Gln  Ser  Asn  Ser  Thr  Asn  Ile  Phe  Phe  Ser  Pro  Val  Ser
 65                 70                      75                           80

Ile  Ala  Thr  Ala  Phe  Ala  Met  Leu  Ser  Leu  Gly  Thr  Lys  Ala  Asp  Thr
                    85                      90                      95

His  Asp  Glu  Ile  Leu  Glu  Gly  Leu  Asn  Phe  Asn  Leu  Thr  Glu  Ile  Pro
               100                     105                     110

Glu  Ala  Gln  Ile  His  Glu  Gly  Phe  Gln  Glu  Leu  Leu  Arg  Thr  Leu  Asn
          115                     120                     125

Gln  Pro  Asp  Ser  Gln  Leu  Gln  Leu  Thr  Thr  Gly  Asn  Gly  Leu  Phe  Leu
     130                     135                     140

Ser  Glu  Gly  Leu  Lys  Leu  Val  Asp  Lys  Phe  Leu  Glu  Asp  Val  Lys  Lys
145                     150                     155                      160

Leu  Tyr  His  Ser  Glu  Ala  Phe  Thr  Val  Asn  Phe  Gly  Asp  Thr  Glu  Glu
               165                     170                     175

Ala  Lys  Lys  Gln  Ile  Asn  Asp  Tyr  Val  Glu  Lys  Gly  Thr  Gln  Gly  Lys
          180                     185                     190

Ile  Val  Asp  Leu  Val  Lys  Glu  Leu  Asp  Arg  Asp  Thr  Val  Phe  Ala  Leu
          195                     200                     205

Val  Asn  Tyr  Ile  Phe  Phe  Lys  Gly  Lys  Trp  Glu  Arg  Pro  Phe  Glu  Val
     210                     215                     220

Lys  Asp  Thr  Glu  Glu  Glu  Asp  Phe  His  Val  Asp  Gln  Val  Thr  Thr  Val
225                     230                     235                      240

Lys  Val  Pro  Met  Met  Lys  Arg  Leu  Gly  Met  Phe  Asn  Ile  Gln  His  Cys
               245                     250                     255
```

```
Lys  Lys  Leu  Ser  Ser  Trp  Val  Leu  Leu  Met  Lys  Tyr  Leu  Gly  Asn  Ala
              260                 265                 270

Thr  Ala  Ile  Phe  Phe  Leu  Pro  Asp  Glu  Gly  Lys  Leu  Gln  His  Leu  Glu
         275                      280                      285

Asn  Glu  Leu  Thr  His  Asp  Ile  Ile  Thr  Lys  Phe  Leu  Glu  Asn  Glu  Asp
     290                      295                      300

Arg  Arg  Ser  Ala  Ser  Leu  His  Leu  Pro  Lys  Leu  Ser  Ile  Thr  Gly  Thr
305                      310                 315                           320

Tyr  Asp  Leu  Lys  Ser  Val  Leu  Gly  Gln  Leu  Gly  Ile  Thr  Lys  Val  Phe
              325                 330                      335

Ser  Asn  Gly  Ala  Asp  Leu  Ser  Gly  Val  Thr  Glu  Glu  Ala  Pro  Leu  Lys
              340                 345                 350

Leu  Ser  Lys  Ala  Val  His  Lys  Ala  Val  Leu  Thr  Ile  Asp  Glu  Lys  Gly
         355                      360                      365

Thr  Glu  Ala  Ala  Gly  Ala  Met  Phe  Leu  Glu  Ala  Ile  Pro  Met  Ser  Ile
     370                      375                 380

Pro  Pro  Glu  Val  Lys  Phe  Asn  Lys  Pro  Phe  Val  Phe  Leu  Met  Ile  Glu
385                      390                      395                      400

Gln  Asn  Thr  Lys  Ser  Pro  Leu  Phe  Met  Gly  Lys  Val  Val  Asn  Pro  Thr
              405                 410                      415

Gln  Lys
```

( 2 ) INFORMATION FOR SEQ ID NO: 4:

( i ) SEQUENCE CHARACTERISTICS:
        ( A ) LENGTH:379
        ( B ) TYPE: amino acid
        ( C ) STRANDEDNESS:
        ( D ) TOPOLOGY: linear ( x i ) SEQUENCE DESCRIPTION: SEQ ID NO: 4:

```
Met  Glu  Gln  Leu  Ser  Ser  Ala  Asn  Thr  Arg  Phe  Ala  Leu  Asp  Leu  Phe
  1            5                      10                      15

Leu  Ala  Leu  Ser  Glu  Asn  Asn  Pro  Ala  Gly  Asn  Ile  Phe  Ile  Ser  Pro
              20                      25                      30

Phe  Ser  Ile  Ser  Ser  Ala  Met  Ala  Met  Val  Phe  Leu  Gly  Thr  Arg  Gly
          35                      40                      45

Asn  Thr  Ala  Ala  Gln  Leu  Ser  Lys  Thr  Phe  His  Phe  Asn  Thr  Val  Glu
     50                      55                      60

Glu  Val  His  Ser  Arg  Phe  Gln  Ser  Leu  Asn  Ala  Asp  Ile  Asn  Lys  Arg
65                      70                      75                       80

Gly  Ala  Ser  Tyr  Ile  Leu  Lys  Leu  Ala  Asn  Arg  Leu  Tyr  Gly  Glu  Lys
              85                      90                      95

Thr  Tyr  Asn  Phe  Leu  Pro  Glu  Phe  Leu  Val  Ser  Thr  Gln  Lys  Thr  Tyr
              100                     105                     110

Gly  Ala  Asp  Leu  Ala  Ser  Val  Asp  Phe  Gln  His  Ala  Ser  Glu  Asp  Ala
         115                     120                      125

Arg  Lys  Thr  Ile  Asn  Gln  Trp  Val  Lys  Gly  Gln  Thr  Glu  Gly  Lys  Ile
         130                     135                      140

Pro  Glu  Leu  Leu  Ala  Ser  Gly  Met  Val  Asp  Asn  Met  Thr  Lys  Leu  Val
145                      150                     155                      160

Leu  Val  Asn  Ala  Ile  Tyr  Phe  Lys  Gly  Asn  Trp  Lys  Asp  Lys  Phe  Met
                   165                     170                     175

Lys  Glu  Ala  Thr  Thr  Asn  Ala  Pro  Phe  Arg  Leu  Asn  Lys  Lys  Asp  Arg
              180                     185                      190
```

-continued

| Lys | Thr | Val 195 | Lys | Met | Met | Tyr | Gln 200 | Lys | Lys | Lys | Phe 205 | Ala | Tyr | Gly | Tyr |
| Ile | Glu 210 | Asp | Leu | Lys | Cys | Arg 215 | Val | Leu | Glu | Leu | Pro 220 | Tyr | Gln | Gly | Glu |
| Glu 225 | Leu | Ser | Met | Val | Ile 230 | Leu | Leu | Pro | Asp | Asp 235 | Ile | Glu | Asp | Glu | Ser 240 |
| Thr | Gly | Leu | Lys | Lys 245 | Ile | Glu | Glu | Gln | Leu 250 | Thr | Leu | Glu | Lys | Leu 255 | His |
| Glu | Trp | Thr | Lys 260 | Pro | Glu | Asn | Leu | Asp 265 | Phe | Ile | Glu | Val | Asn 270 | Val | Ser |
| Leu | Pro | Arg 275 | Phe | Lys | Leu | Glu | Glu 280 | Ser | Tyr | Thr | Leu | Asn 285 | Ser | Asp | Leu |
| Ala | Arg 290 | Leu | Gly | Val | Gln | Asp 295 | Leu | Phe | Asn | Ser | Ser 300 | Lys | Ala | Asp | Leu |
| Ser 305 | Gly | Met | Ser | Gly | Ala 310 | Arg | Asp | Ile | Phe | Ile 315 | Ser | Lys | Ile | Val | His 320 |
| Lys | Ser | Phe | Val | Glu 325 | Val | Asn | Glu | Glu | Gly 330 | Thr | Glu | Ala | Ala | Ala 335 | Ala |
| Thr | Ala | Gly | Ile 340 | Ala | Thr | Phe | Cys | Met 345 | Leu | Met | Pro | Glu | Glu 350 | Asn | Phe |
| Thr | Ala | Asp 355 | His | Pro | Phe | Leu | Phe 360 | Phe | Ile | Arg | His | Asn 365 | Ser | Ser | Gly |
| Ser | Ile 370 | Leu | Phe | Leu | Gly | Arg 375 | Phe | Ser | Ser | Pro | | | | | |

( 2 ) INFORMATION FOR SEQ ID NO: 5:

( i ) SEQUENCE CHARACTERISTICS:
        ( A ) LENGTH:375
        ( B ) TYPE: amino acid
        ( C ) STRANDEDNESS:
        ( D ) TOPOLOGY: linear ( x i ) SEQUENCE DESCRIPTION: SEQ ID NO: 5:

| Gly 1 | Ser | Ile | Gly | Ala 5 | Ala | Ser | Met | Glu | Phe 10 | Cys | Phe | Asp | Val | Phe 15 | Lys |
| Glu | Leu | Lys | Val 20 | His | His | Ala | Asn | Glu 25 | Asn | Ile | Phe | Tyr | Cys 30 | Pro | Ile |
| Ala | Ile | Met 35 | Ser | Ala | Leu | Ala | Met 40 | Val | Tyr | Leu | Gly | Ala 45 | Lys | Asp | Ser |
| Thr | Arg 50 | Thr | Gln | Ile | Asn | Lys 55 | Val | Val | Arg | Phe | Asp 60 | Lys | Leu | Pro | Gly |
| Phe 65 | Gly | Asp | Ser | Ile | Glu 70 | Ala | Gln | Cys | Gly | Thr 75 | Ser | Val | Asn | Val | His 80 |
| Ser | Ser | Leu | Arg | Asp 85 | Ile | Leu | Asn | Gln | Ile 90 | Thr | Lys | Pro | Asn | Asp 95 | Val |
| Tyr | Ser | Phe | Ser 100 | Leu | Ala | Ser | Arg | Leu 105 | Tyr | Ala | Glu | Glu | Arg 110 | Tyr | Pro |
| Ile | Leu | Pro 115 | Glu | Tyr | Leu | Gln | Cys 120 | Val | Lys | Glu | Leu | Tyr 125 | Arg | Gly | Gly |
| Leu | Glu 130 | Pro | Ile | Asn | Phe | Gln 135 | Thr | Ala | Ala | Asp | Gln 140 | Ala | Arg | Glu | Leu |
| Ile 145 | Asn | Ser | Trp | Val | Glu 150 | Ser | Gln | Thr | Asn | Gly 155 | Ile | Ile | Arg | Asn | Val 160 |
| Leu | Gln | Pro | Ser | Ser 165 | Val | Asp | Ser | Gln | Thr 170 | Ala | Met | Val | Leu | Val 175 | Asn |

```
Ala  Ile  Val  Phe  Lys  Gly  Leu  Trp  Glu  Lys  Ala  Phe  Lys  Asp  Glu  Asp
               180                      185                      190

Thr  Gln  Ala  Met  Pro  Phe  Arg  Val  Thr  Glu  Gln  Glu  Ser  Lys  Pro  Val
          195                      200                      205

Gln  Met  Met  Tyr  Gln  Ile  Gly  Leu  Phe  Arg  Val  Ala  Ser  Met  Ala  Ser
     210                      215                      220

Glu  Lys  Met  Lys  Ile  Leu  Glu  Leu  Pro  Phe  Ala  Ser  Gly  Thr  Met  Ser
225                      230                      235                      240

Met  Leu  Val  Leu  Leu  Pro  Asp  Glu  Val  Ser  Gly  Leu  Glu  Gln  Leu  Glu
               245                      250                      255

Ser  Ile  Ile  Asn  Phe  Glu  Lys  Leu  Thr  Glu  Trp  Thr  Ser  Ser  Asn  Val
               260                      265                      270

Met  Glu  Glu  Arg  Lys  Ile  Lys  Val  Tyr  Leu  Pro  Arg  Met  Lys  Met  Glu
          275                      280                      285

Glu  Lys  Tyr  Asn  Leu  Thr  Ser  Val  Leu  Met  Ala  Met  Gly  Ile  Thr  Asp
     290                      295                      300

Val  Phe  Ser  Ser  Ser  Ala  Asn  Leu  Ser  Gly  Ile  Ser  Ser  Ala  Glu  Ser
305                      310                      315                      320

Leu  Lys  Ile  Ser  Gln  Ala  Val  His  Ala  Ala  His  Ala  Glu  Ile  Asn  Glu
               325                      330                      335

Ala  Gly  Arg  Glu  Val  Val  Gly  Ser  Ala  Glu  Ala  Gly  Val  Asp  Ala  Ala
          340                      345                      350

Ser  Val  Ser  Glu  Glu  Phe  Arg  Ala  Asp  His  Pro  Phe  Leu  Phe  Cys  Ile
          355                      360                      365

Lys  His  Ile  Ala  Thr  Asn  Ala
     370                      375
```

( 2 ) INFORMATION FOR SEQ ID NO: 6:

( i ) SEQUENCE CHARACTERISTICS:
        ( A ) LENGTH:390
        ( B ) TYPE: amino acid
        ( C ) STRANDEDNESS:
        ( D ) TOPOLOGY: linear ( x i ) SEQUENCE DESCRIPTION: SEQ ID NO: 6:

```
Met  Gln  Met  Ser  Pro  Ala  Leu  Thr  Cys  Leu  Val  Leu  Gly  Leu  Ala  Ile
 1                  5                       10                       15

Val  Phe  Gly  Glu  Gly  Ser  Ala  Val  His  His  Pro  Pro  Ser  Tyr  Val  Ala
               20                       25                       30

His  Leu  Ala  Ser  Asp  Phe  Gly  Val  Arg  Val  Phe  Gln  Gln  Val  Ala  Gln
          35                       40                       45

Ala  Ser  Lys  Asp  Arg  Asn  Val  Val  Phe  Ser  Pro  Tyr  Gly  Val  Ala  Ser
     50                       55                       60

Val  Leu  Ala  Met  Leu  Gln  Leu  Thr  Thr  Gly  Gly  Glu  Thr  Gln  Gln  Gln
65                       70                       75                       80

Ile  Gln  Ala  Ala  Met  Gly  Phe  Lys  Ile  Asp  Asp  Lys  Gly  Met  Ala  Pro
                85                       90                       95

Ala  Leu  Arg  His  Leu  Tyr  Lys  Glu  Leu  Met  Gly  Pro  Trp  Asn  Lys  Asp
          100                      105                      110

Glu  Ile  Ser  Thr  Thr  Asp  Ala  Ile  Phe  Val  Gln  Arg  Asp  Leu  Lys  Leu
     115                      120                      125

Val  Gln  Gly  Phe  Met  Pro  His  Phe  Phe  Arg  Leu  Phe  Arg  Ser  Thr  Val
130                      135                      140

Lys  Gln  Val  Asp  Phe  Ser  Glu  Val  Glu  Arg  Ala  Arg  Phe  Ile  Ile  Asn
145                      150                      155                      160
```

-continued

| | | | | | | | | | | | | | | |
|---|---|---|---|---|---|---|---|---|---|---|---|---|---|---|
|Asp|Trp|Val|Lys|Thr<br>165|His|Thr|Lys|Gly|Met<br>170|Ile|Ser|Asn|Leu|Leu<br>175|Gly|
|Lys|Gly|Ala|Val<br>180|Asp|Gln|Leu|Thr|Arg<br>185|Leu|Val|Leu|Val|Asn<br>190|Ala|Leu|
|Tyr|Phe|Asn<br>195|Gly|Gln|Trp|Lys|Thr<br>200|Pro|Phe|Pro|Asp|Ser<br>205|Ser|Thr|His|
|Arg|Arg<br>210|Leu|Phe|His|Lys|Ser<br>215|Asp|Gly|Ser|Thr|Val<br>220|Ser|Val|Pro|Met|
|Met<br>225|Ala|Gln|Thr|Asn|Lys<br>230|Phe|Asn|Tyr|Thr|Glu<br>235|Phe|Thr|Thr|Pro|Asp<br>240|
|Gly|His|Tyr|Tyr|Asp<br>245|Ile|Leu|Glu|Leu|Pro<br>250|Tyr|His|Gly|Asp|Thr<br>255|Leu|
|Ser|Met|Phe|Ile<br>260|Ala|Ala|Pro|Tyr|Glu<br>265|Lys|Glu|Val|Pro|Leu<br>270|Ser|Ala|
|Leu|Thr|Asn<br>275|Ile|Leu|Ser|Ala|Gln<br>280|Leu|Ile|Ser|His|Trp<br>285|Lys|Gly|Asn|
|Met|Thr<br>290|Arg|Leu|Pro|Arg|Leu<br>295|Leu|Val|Leu|Pro|Lys<br>300|Phe|Ser|Leu|Glu|
|Thr<br>305|Glu|Val|Asp|Leu|Arg<br>310|Lys|Pro|Leu|Glu|Asn<br>315|Leu|Gly|Met|Thr|Asp<br>320|
|Met|Phe|Arg|Gln|Phe<br>325|Gln|Ala|Asp|Phe|Thr<br>330|Ser|Leu|Ser|Asp|Gln<br>335|Glu|
|Pro|Leu|His|Val<br>340|Ala|Gln|Ala|Leu|Gln<br>345|Lys|Val|Lys|Ile|Glu<br>350|Val|Asn|
|Glu|Ser|Gly<br>355|Thr|Val|Ala|Ser|Ser<br>360|Ser|Thr|Ala|Val|Ile<br>365|Val|Ser|Ala|
|Arg|Met<br>370|Ala|Pro|Glu|Glu|Ile<br>375|Ile|Met|Asp|Arg|Pro<br>380|Phe|Leu|Phe|Val|
|Val<br>385|Arg|His|Asn|Pro|Thr<br>390| | | | | | | | | | |

( 2 ) INFORMATION FOR SEQ ID NO: 7:

( i ) SEQUENCE CHARACTERISTICS:
        ( A ) LENGTH: 405
        ( B ) TYPE: amino acid
        ( C ) STRANDEDNESS:
        ( D ) TOPOLOGY: linear ( x i ) SEQUENCE DESCRIPTION: SEQ ID NO: 7:

| | | | | | | | | | | | | | | |
|---|---|---|---|---|---|---|---|---|---|---|---|---|---|---|
|Met<br>1|Glu|Asp|Leu|Cys<br>5|Val|Ala|Asn|Thr|Leu<br>10|Phe|Ala|Leu|Asn|Leu<br>15|Phe|
|Lys|His|Leu|Ala<br>20|Lys|Ala|Ser|Pro|Thr<br>25|Gln|Asn|Leu|Phe|Leu<br>30|Ser|Pro|
|Trp|Ser|Ile<br>35|Ser|Ser|Thr|Met|Ala<br>40|Met|Val|Tyr|Met|Gly<br>45|Ser|Arg|Gly|
|Ser|Thr<br>50|Glu|Asp|Gln|Met|Ala<br>55|Lys|Val|Leu|Gln|Phe<br>60|Asn|Glu|Val|Gly|
|Ala<br>65|Asn|Ala|Val|Thr|Pro<br>70|Met|Thr|Pro|Glu|Asn<br>75|Phe|Thr|Ser|Cys|Gly<br>80|
|Phe|Met|Gln|Gln|Ile<br>85|Gln|Lys|Gly|Ser|Tyr<br>90|Pro|Asp|Ala|Ile|Leu<br>95|Gln|
|Ala|Gln|Ala|Ala<br>100|Asp|Lys|Ile|His|Ser<br>105|Ser|Phe|Arg|Ser|Leu<br>110|Ser|Ser|
|Ala|Ile|Asn|Ala<br>115|Ser|Thr|Gly|Asp|Tyr<br>120|Leu|Leu|Glu|Ser|Val<br>125|Asn|Lys|Lys|

| | | | | | | | | | | | | | |
|---|---|---|---|---|---|---|---|---|---|---|---|---|---|
| Leu | Phe 130 | Gly | Glu | Lys | Ser 135 | Ala | Ser | Phe | Arg | Glu 140 | Tyr | Ile | Arg | Leu |
| Cys 145 | Gln | Lys | Tyr | Tyr | Ser 150 | Ser | Glu | Pro | Gln | Ala 155 | Val | Asp | Phe | Leu | Glu 160 |
| Cys | Ala | Glu | Glu | Ala 165 | Arg | Lys | Lys | Ile | Asn 170 | Ser | Trp | Val | Lys | Thr 175 | Gln |
| Thr | Lys | Gly | Lys 180 | Ile | Pro | Asn | Leu | Leu 185 | Pro | Glu | Gly | Ser | Val 190 | Asp | Gly |
| Asp | Thr | Arg 195 | Met | Val | Leu | Val | Asn 200 | Ala | Val | Tyr | Phe | Lys 205 | Gly | Lys | Trp |
| Lys | Thr 210 | Pro | Phe | Glu | Lys 215 | Lys | Leu | Asn | Gly | Leu 220 | Tyr | Pro | Phe | Arg | Val |
| Asn 225 | Ser | Ala | Gln | Arg | Thr 230 | Pro | Val | Gln | Met | Met 235 | Tyr | Leu | Arg | Glu | Lys 240 |
| Leu | Asn | Ile | Gly | Tyr 245 | Ile | Glu | Asp | Leu | Lys 250 | Ala | Gln | Ile | Leu | Glu 255 | Leu |
| Pro | Tyr | Ala | Gly 260 | Asp | Val | Ser | Met | Phe 265 | Leu | Leu | Leu | Pro | Asp 270 | Glu | Ile |
| Ala | Asp | Val 275 | Ser | Thr | Gly | Leu | Glu 280 | Leu | Leu | Glu | Ser | Glu 285 | Ile | Thr | Tyr |
| Asp | Lys 290 | Leu | Asn | Lys | Trp | Thr 295 | Ser | Lys | Asp | Lys | Met 300 | Ala | Glu | Asp | Glu |
| Val 305 | Glu | Val | Tyr | Ile | Pro 310 | Gln | Phe | Lys | Leu | Glu 315 | Glu | His | Tyr | Glu | Leu 320 |
| Arg | Ser | Ile | Leu | Arg 325 | Ser | Met | Gly | Met | Asp 330 | Ala | Phe | Asn | Lys 335 | Gly |
| Arg | Ala | Asn | Phe 340 | Ser | Gly | Met | Ser | Glu 345 | Arg | Asn | Asp | Leu | Phe 350 | Leu | Ser |
| Glu | Val | Phe 355 | His | Gln | Ala | Met | Val 360 | Asp | Val | Asn | Glu | Glu 365 | Gly | Thr | Glu |
| Ala | Ala 370 | Ala | Gly | Thr | Gly | Gly 375 | Val | Met | Thr | Gly | Arg 380 | Thr | Gly | His | Gly |
| Gly 385 | Pro | Gln | Phe | Val | Ala 390 | Asp | His | Pro | Phe | Leu 395 | Phe | Leu | Ile | Met | His 400 |
| Lys | Ile | Thr | Lys | Cys 405 | | | | | | | | | | | |

( 2 ) INFORMATION FOR SEQ ID NO: 8:

( i ) SEQUENCE CHARACTERISTICS:
        ( A ) LENGTH: 375
        ( B ) TYPE: amino acid
        ( C ) STRANDEDNESS:
        ( D ) TOPOLOGY: linear ( x i ) SEQUENCE DESCRIPTION: SEQ ID NO: 8:

| | | | | | | | | | | | | | | | |
|---|---|---|---|---|---|---|---|---|---|---|---|---|---|---|---|
| Met 1 | Glu | Gln | Leu | Ser 5 | Thr | Ala | Asn | Thr | His 10 | Phe | Ala | Val | Asp | Leu 15 | Phe |
| Arg | Ala | Leu | Asn 20 | Glu | Ser | Asp | Pro | Thr 25 | Gly | Asn | Ile | Phe | Ile 30 | Ser | Pro |
| Leu | Ser | Ile 35 | Ser | Ser | Ala | Leu | Ala 40 | Met | Ile | Phe | Leu | Gly 45 | Thr | Arg | Gly |
| Asn | Thr 50 | Ala | Ala | Gln | Val | Ser 55 | Lys | Ala | Leu | Tyr | Phe 60 | Asp | Thr | Val | Glu |
| Asp 65 | Ile | His | Ser | Arg | Phe 70 | Gln | Ser | Leu | Asn | Ala 75 | Asp | Ile | Asn | Lys | Pro 80 |

-continued

```
Gly Ala Pro Tyr Ile Leu Lys Leu Ala Asn Arg Leu Tyr Gly Glu Lys
                 85                  90                  95
Thr Tyr Asn Phe Leu Ala Asp Phe Leu Ala Ser Thr Gln Lys Met Tyr
            100                 105                 110
Gly Ala Glu Leu Ala Ser Val Asp Phe Gln Gln Ala Pro Glu Asp Ala
            115                 120                 125
Arg Lys Glu Ile Asn Glu Trp Val Lys Gly Gln Thr Glu Gly Lys Ile
        130                 135                 140
Pro Glu Leu Leu Val Lys Gly Met Val Asp Asn Met Thr Lys Leu Val
145                 150                 155                 160
Leu Val Asn Ala Ile Tyr Phe Lys Gly Asn Trp Gln Glu Lys Phe Met
                165                 170                 175
Lys Glu Ala Thr Arg Asp Ala Pro Phe Arg Leu Asn Lys Lys Asp Thr
            180                 185                 190
Lys Thr Val Lys Met Met Tyr Gln Lys Lys Phe Pro Tyr Asn Tyr
            195                 200                 205
Ile Glu Asp Leu Lys Cys Arg Val Leu Glu Leu Pro Tyr Gln Gly Lys
        210                 215                 220
Glu Leu Ser Met Ile Ile Leu Leu Pro Asp Asp Ile Glu Asp Glu Ser
225                 230                 235                 240
Thr Gly Leu Glu Lys Ile Glu Lys Gln Leu Thr Leu Glu Lys Leu Arg
                245                 250                 255
Glu Trp Thr Lys Pro Glu Asn Leu Tyr Leu Ala Glu Val Asn Val His
            260                 265                 270
Leu Pro Arg Phe Lys Leu Glu Glu Ser Tyr Asp Leu Thr Ser His Leu
        275                 280                 285
Ala Arg Leu Gly Val Gln Asp Leu Phe Asn Arg Gly Lys Ala Asp Leu
290                 295                 300
Ser Gly Met Ser Gly Ala Arg Asp Leu Phe Val Ser Lys Ile Ile His
305                 310                 315                 320
Lys Ser Phe Val Asp Leu Asn Glu Glu Gly Thr Glu Ala Ala Ala Ala
                325                 330                 335
Thr Ala Gly Thr Ile Met Leu Ala Met Leu Met Pro Glu Glu Asn Phe
            340                 345                 350
Asn Ala Asp His Pro Phe Ile Phe Phe Ile Arg His Asn Pro Ser Ala
        355                 360                 365
Asn Ile Leu Phe Leu Gly Arg
370                 375
```

( 2 ) INFORMATION FOR SEQ ID NO: 9:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 9:

```
Tyr Ala Lys Glu Leu Glu Thr Val Asp Phe Lys Asp Lys Leu Glu
 1               5                  10                  15
```

( 2 ) INFORMATION FOR SEQ ID NO: 10:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear (xi) SEQUENCE DESCRIPTION: SEQ ID NO: 10:

Gly Lys Trp Met Lys Lys Phe Pro Glu Ser Glu Thr Lys Glu
 1               5                  10

(2) INFORMATION FOR SEQ ID NO: 11:

(i) SEQUENCE CHARACTERISTICS:
 (A) LENGTH: 15
 (B) TYPE: amino acid
 (C) STRANDEDNESS:
 (D) TOPOLOGY: linear (xi) SEQUENCE DESCRIPTION: SEQ ID NO: 11:

Ile Glu Val Pro Gly Ala Arg Ile Leu Gln His Lys Asp Glu Leu
 1               5                  10                  15

METHOD OF DETECTING CANCER

This application is a divisional of application Ser. No. 08/121,714, filed Sep. 1, 1993, now issued as U.S. Pat. No. 5,470,970, which is a a continuation-in-part of currently pending U.S. application Ser. No. 07/938,823 (herein incorporated by reference), which was filed Sep. 1, 1992, now abandoned, and is commonly owned with the present application, and which in turn is a continuation-in-part of U.S. application Ser. No. 07/844,296, filed Feb. 28, 1992, now abandoned, which in turn is a continuation-in-part of U.S. application Ser. No. 07/662,216, filed Feb. 28, 1991, now abandoned.

STATEMENT AS TO FEDERALLY SPONSORED RESEARCH

The invention described herein was made in part with the support of the U.S. Government (NIH grant nos. P01 CA22427 and OIG CA39814 to Dr. Ruth Sager). The U.S. Government therefore has certain rights in the invention.

BACKGROUND OF THE INVENTION

The field of the invention is tumor suppressor genes.

Cancer at the cellular level is characterized by the disruption of multiple regulatory mechanisms resulting from multiple genetic changes. The search for specific genes with major cancer-related effects has focussed on two fundamental processes: control of proliferation, and control of invasion and metastatic spread. Both processes are complex, and the relevant cancer-related changes in gene expression involve both increases and decreases in the activity of particular proteins.

Metastatic spread occurs when primary tumor cells invade into lymphatics and blood vessels, and disseminate to distant organs (Fidler et al., J. Natl. Cancer Inst. 82:166, 1990; Liotta et al., Cancer Res. 51:5054, 1991; Nicolson, Semin. Cancer Biol. 2:143, 1991; and Chen, Current Opin. Cell Biol. 4:802, 1992). The multiple steps involved in metastasis include proteolytic attack on the basement membrane and extracellular matrix (ECM), adhesion to endothelial cells leading to intravasation, and later extravasation from the circulatory system into tissues such as lung and bone in which the tumor cells are able to proliferate. In normal cells, these processes of invasion and metastasis are blocked by an intricate array of genetically programmed regulatory mechanisms. Overcoming these protective barriers to invasion and metastasis requires multiple changes in gene expression, resulting in gain or loss of gene functions that contribute to tumor progression.

Increased proteolytic activity augments invasion, as evidenced by the increased activity of serine proteases (Testa et al., Cancer Metastasis Rev. 9:353, 1990; Dano et al., Adv. Cancer Res. 44:139, 1985; Foekens et al., Cancer Res. 52:6101, 1992; Ossowsky, Cancer Res. 52:6754, 1992; Sumiyoshi, Int. J. Cancer 50:345, 1992; Duffy et al., Cancer Res. 50:6827, 1992; and Meissauer et al., Exp. Cell Res. 192:453, 1991, metalloproteases (Birkedal-Hansen (ed) Proceedings of the Matrix Metalloporteinase Conference, Destin, Florida, Gustav Fischer Verlag, 1990; Matrisian et al., Am. J. Med. Sci. 302:157, 1991; Stetler-Stevenson, Cancer Metastasis Rev. 9:289, 1990; DeClerck et al., Cancer Res. 52:701, 1992; Bassett, Nature 348:699, 1990; Wolf et al., Proc. Natl. Acad. Sci. USA 90:1843, 1993; and Sato et al., Oncogene 7:77, 1992), and cathepsins (Rochefort et al., Cancer Metast. Rev. 9:321, 1990; and Kobayashi et al., Cancer Res. 52:3610, 1992) in invasive tumor cells. The principal serine proteases known to be associated with tumor invasion mediate the plasminogen activation cascade. In this pathway, plasminogen is converted by plasminogen activators to plasmin, which is a wide-spectrum serine protease that degrades many components of the ECM directly, or indirectly via the activation of metalloproteases. The activity of the plasminogen activators is negatively regulated by plasminogen activator inhibitory proteins: PAI-1, PAI-2, and protease nexins (Chen, Current Opin. Cell Biol. 4:802, 1992).

The elevated expression of uPA (urokinase plasminogen activator) in breast carcinomas and other cancers has been reported by numerous investigators since the 1970's (Testa et al., Cancer Metastasis Rev. 9:353, 1990; Dano et al., Adv. Cancer Res. 44:139, 1985; Foekens et al., Cancer Res. 52:6101, 1992; Ossowsky, Cancer Res. 52:6754, 1992; Sumiyoshi, Int. J. Cancer 50:345, 1992; Duffy et al., Cancer Res. 50:6827, 1992; and Meissauer et al., Exp. Cell Res. 192:453, 1991; Heidtmann et al., Cancer Res. 49:6960, 1989; Sumiyoshi et al., Thromb Res. 63:59, 1991; Reilly et al., Int. J. Cancer 50:208, 1992, Cajot et al., Proc. Natl. Acad. Sci. USA 87:6939, 1990; Foucre et al., Br. J. Cancer 64:926, 1991; Shirasuna et al., Cancer Res. 53:147, 1993; and Janicke et al., Br. Can. Res. & Treat. 24:195, 1993). More recently, it has been shown that PAI-1 and PAI-2 are also elevated in malignancy (Sumiyoshi, Int. J. Cancer 50:345, 1992; Heidtmann et al., Cancer Res. 49:6960, 1989; Sumiyoshi et al., Thromb Res. 63:59, 1991; Reilly et al., Int. J. Cancer 50:208, 1992, Cajot et al., Proc. Natl. Acad. Sci. USA 87:6939, 1990; Foucre et al., Br. J. Cancer 64:926, 1991; Shirasuna et al., Cancer Res. 53:147, 1993; and Janicke et al., Br. Can. Res. & Treat. 24:195, 1993). These findings are inconsistent with the simple paradigm of protease/antiprotease balance in normal cells and its imbalance in tumor cells, thus confusing the issue of how effective uPA may be in metastatic dissemination. Recent studies of the uPA receptor and its importance in modulating uPA activity (Testa et al., Cancer Metastasis Rev. 9:353, 1990; Vassalli et al., J. Cell Biol. 100:86, 1985; and Lund et al., EMBO J. 10:3399, 1991) have indicated further levels of regulation. Thus, although it has been clearly established that uPA is capable of degrading components of the basement membrane and ECM, and that it is often elevated in advanced breast cancer, its precise role in breast cancer invasion remains to be established. Similarly, the importance of PAI-1 and PAI-2 in inhibiting breast cancer invasion is not clearly established (Testa et al., Cancer Metastasis Rev. 9:353, 1990).

The matrix metalloproteases (MMPs) include collagenases and stromelysins. The type IV collagenases (gelatinases), in particular the 72 kDa form, are active in tumor invasion, as indicated by elevated levels in aggressive human tumors (Stetler-Stevenson, Cancer Metastasis Rev. 9:289, 1990). The tissue inhibitors of metalloproteinase activity, TIMP-1 and TIMP-2, target the type IV collagenases, with TIMP-2 interacting exclusively with the 72 kDa form (Stetler-Stevenson et al., Annu. Rev. Cell Biol. 9:541, 1993). Stromelysins-1 (transin) and -2 have been associated with tumor progression in rodent systems, whereas a smaller molecule called PUMP has been identified in human tumor cells (Matrisian et al., Am. J. Med. Sci. 302:157, 1991). Extensive studies of stromelysin-3 have shown a strong correlation with advanced breast cancer (Bassett, Nature 348:699, 1990; Wolf et al., Proc. Natl. Acad. Sci. USA 90:1843, 1993). This protease is secreted by stromal fibroblasts that are proximal to invasive primary breast carcinomas, and not by the epithelial tumor cells,

SUMMARY OF THE INVENTION

Disclosed herein is a new gene, originally isolated by subtractive hybridization, that is involved in protection against a primary step in the metastatic cascade. The gene, called maspin, encodes a novel serine protease inhibitor expressed in normal mammary epithelial cells in culture and in the normal breast. Its expression decreases during progression from well-differentiated to poorly differentiated primary carcinomas, and is absent in most lymph node and distant metastatic lesions. The inferred structure of the protein is consistent with serine protease inhibitor activity. Functional studies indicate that the protein has tumor suppressing and invasion suppressing activity.

The invention thus includes an isolated DNA encoding a polypeptide substantially identical to maspin (i.e., having at least 90% sequence identity to SEQ ID NO:2, with any amino acid substitutions preferably being conservative), or to an allelic variant of SEQ ID NO:2, or to a homolog of maspin from a species other than man. The isolated DNA preferably contains a DNA sequence which hybridizes under stringent conditions (as defined below) with the DNA sequence of SEQ ID NO:1, or the complement thereof, and may contain the sequence of SEQ ID NO:1. It is preferably incorporated into a vector (a virus, phage, or plasmid) which can be introduced by transfection or infection into a cell. The vector preferably includes one or more expression control sequences, in which case the cell transfected by the vector is capable of expressing the polypeptide. By "isolated DNA" is meant a single- or double-stranded DNA that is free of the genes which, in the naturally-occurring genome of the animal from which the isolated DNA is derived, flank the maspin gene. The term therefore includes, for example, either or both strands of a cDNA encoding maspin or an allelic variant thereof; a recombinant DNA which is incorporated into a vector, into an autonomously replicating plasmid or virus, or into the genomic DNA of a prokaryotic or eukaryotic cell; or a genomic DNA fragment (e.g., produced by PCR [polymerase chain reaction] or restriction endonuclease treatment of human or other genomic DNA). It also includes a recombinant DNA which is part of a hybrid gene encoding additional polypeptide sequence.

Stringent conditions for both DNA/DNA and DNA/RNA hybridization assays are as described by Sambrook et al., *Molecular Cloning, A Laboratory Manual*, 2nd Ed., Cold Spring Harbor Laboratory Press, Cold Spring Harbor, N.Y., 1989, herein incorporated by reference. For example, see page 7.52 of Sambrook et al.

Also within the invention is an isolated DNA at least 15 nucleotides in length (preferably at least 30, more preferably at least 100, and most preferably at least 500), including (a) a strand which hybridizes under stringent conditions to a DNA having the sequence of SEQ ID NO:1, (b) the complement thereof, or (c) a double stranded DNA including both (a) and (b). Multiple copies of this isolated DNA (useful, for example, as a hybridization probe or PCR primer) can be produced by recombinant means, by transfecting a cell with a vector containing this DNA.

The invention also includes a purified preparation of maspin protein (SEQ ID NO:1), or a fragment of maspin that is an antigenic polypeptide containing from 10 to 374 amino acid residues of maspin (preferably at least 12, more preferably at least 14, and most preferably at least 18 (e.g., 20 or more), which polypeptide fragment contains an epitope of maspin such that an antibody raised against the fragment (or against a conjugate of the polypeptide and keyhole limpet hemocyanin) forms an immune complex with maspin itself. Such an antibody may be either polyclonal or monoclonal, and is generated by standard methods including the step of immunizing an animal with an antigen containing an antigenic portion of maspin. Also within the invention are hybrid polypeptides containing (1) maspin or an antigenic fragment thereof, covalently attached to (2) a second polypeptide. Such hybrid polypeptides can be made by any of a number of standard techniques well known to those of ordinary skill, including recombinant methods, in which case the covalent attachment is a peptide bond, or chemical conjugation, in which case the covalent attachment is another type of bond, such as a disulfide bond. Linking maspin or an antigenic fragment thereof to a second polypeptide provides a means for readily isolating the hybrid from a mixture of proteins, by the use of an affinity column to which the second polypeptide (e.g., glutathione transferase) binds directly. Such hybrid polypeptides may also have the advantage of increased immunogenicity relative to maspin or the maspin fragment, so that antibodies are more readily obtained.

Both the isolated DNAs of the invention and the antibodies of the invention are useful in diagnostic methods for detecting carcinomas, or for staging a carcinoma, where the suspected carcinoma is derived from a type of cell which normally expresses the maspin gene to a significant and easily detectable degree (e.g., mammary epithelial cells). One such diagnostic method includes the steps of providing a test cell (e.g., in the form of a tissue section or a cell preparation) from a given type of epithelial tissue; contacting the mRNA of the test cell with a nucleic acid probe containing a sequence antisense to (i.e., complementary to the sense strand of) a segment of SEQ ID NO:1, which segment is at least 15 (preferably at least 20, more preferably at least 30, even more preferably at least 40, and most preferably at least 100) nucleotides in length; and comparing (1) the amount of hybridization of the probe to the mRNA of the test cell, with (2) the amount of hybridization of the probe to the mRNA of a normal control (i.e., non-cancerous) cell from the same type of epithelial tissue, wherein an amount of hybridization to the mRNA of the test cell substantially less than the amount obtained with the mRNA of the normal control cell (preferably less than about one-half, more preferably less than about one-third, and more preferably less than about one-tenth the control amount of hybridization) is an indication that the test cell is cancerous. An absence of hybridization with the mRNA of the test cell is an indication that the test cell is from an advanced, probably metastatic tumor, while an amount of hybridization that is detectable but substantially less (e.g., one-third or less) than that measured in a normal cell of the same tissue type is an indication that the test cell is from an early stage carcinoma that is probably not yet metastatic. The assay can be conveniently carried out using standard techniques of in situ hybridization or Northern analysis.

The antibody-based assays of the invention are comparable to the above. The proteins of the test cell, or from a fluid bathing the test cell, are contacted with an antibody (polyclonal or monoclonal) specific for maspin, and the amount of immunocomplex formed with such proteins is compared with the amount formed by the same antibody with the proteins of a normal control cell (or from a fluid bathing the normal control cell) from the same type of epithelial tissue as the test cell. An amount of immunocomplex observed with the proteins of the test cell substantially less than the amount observed with the proteins of the normal control cell (e.g., less than about one-half, preferably less than about one-third, and more preferably less than about one-tenth) is an indication that the test cell is cancerous. The absence of consistently detectable immunocomplex formed with the proteins of the test cell is an indication that the test cell is from an advanced, probably metastatic tumor, while an amount of immunocomplex formation that is consistently detectable but less (e.g., one-third or less) than that measured in a normal cell of the same tissue type is an indication that the test cell is from an early stage carcinoma that is probably not yet metastatic. (By consistently detectable is meant that, in all or nearly all of repeated trials, an amount greater than the applicable background level is observed.)

The immunoassay of the invention alternatively can be carried out on a biological fluid, since maspin protein is normally secreted by epithelial tissues such as mammary tissue. Such an assay would require obtaining a sample of a biological fluid (e.g., blood, serum, urine, saliva, milk, ductal fluid, tears, or semen) from an individual, which biological fluid would, in an individual free of carcinoma, contain a control amount of maspin. The sample, or protein derived from the sample, is contacted with the anti-maspin antibody, and the amount of immunocomplex formed is determined. This amount indicates the concentration or amount of maspin in the biological fluid. When compared to a sample previously or subsequently obtained from the same individual, this method provides a way to monitor the appearance, progress, or treatment of a carcinoma.

In another aspect, the invention features a method for screening candidate anticancer compounds, using as a screening tool cells (e.g., primary cells or an established cell line) from a carcinoma derived from a given tissue type in which the maspin gene is intact but down-regulated: that is, the level of expression of maspin in that carcinoma is significantly lower than (e.g., less than one-third of) the level of expression in normal epithelial cells from that type of tissue. The tissue may be from a human or another animal, and is preferably mammary epithelium. It is preferred that there be no detectable expression of maspin in the cells to be employed in the screen: i.e., the maspin gene is entirely shut down. The screening method includes the step of providing two samples of the screening cells, one of which is treated with a candidate anticancer compound and the other of which serves as control. The level of expression of maspin in the treated sample is compared with the level in the second sample, a higher level in the first sample being an indication that the candidate compound is a potential anticancer agent. The level of expression can be determined by use of hybridization methods or by immunoassay, as described herein.

As an alternative way of screening for potential anticancer agents, one can use any cell in which expression of maspin is undetectable, but which contains an intact maspin gene. This cell would be treated with a candidate anticancer compound, and a determination made of whether expression of maspin is thereby increased in the cell. Such an increase of maspin expression is an indication that the candidate compound is a potential anticancer agent. As above, the level of expression can be determined by use of hybridization methods or by immunoassay.

Also within the invention are methods of treating a carcinoma, where the carcinoma is one in which expression of maspin is decreased relative to normal cells of the tissue type from which the carcinoma cells were derived. In these methods, the patient is treated with an effective amount of a compound which increases the amount of maspin in, or in the immediate vicinity of, his or her carcinoma cells. This compound could be, for example, maspin or a biologically active fragment thereof; a nucleic acid encoding maspin and having expression control elements permitting expression in the carcinoma cells; or an agent which increases the level of expression of a maspin gene endogenous to the carcinoma cells (i.e., which up-regulates expression of the maspin gene).

The invention also features methods for in vivo screening of candidate anticancer agents, or for determining whether a particular carcinoma, in which maspin expression is down-regulated in comparison with normal cells of the same tissue type, is treatable with a given compound that increases expression of maspin. Such a method would include the steps of (1) introducing a carcinoma cell (e.g., a from a mammary carcinoma) into a severely immunodeficient animal (e.g. a nude mouse), the expression of maspin (SEQ ID NO:2) in the cell being down-regulated in comparison with that in a normal cell of the same type of tissue as the carcinoma cell; (2) treating the animal with a compound which increases the concentration of maspin in or around (i.e., in the immediate vicinity of) the carcinoma cell; and (3) determining whether this treatment affects the rate of proliferation or metastasis of the carcinoma cell in the animal, wherein a decrease in the rate of proliferation or metastasis in the presence of the compound is an indication that (a) the compound is potentially useful for treatment of carcinomas, and (b) the carcinoma from which the cell is derived is potentially treatable with the compound.

Besides the in vivo assay described above, one can also utilize an in vitro assay for carcinoma cell invasive capacity based upon the assay described in detail below. Such an assay would include the steps of (1) providing a first and a second carcinoma cell, which cells express maspin (SEQ ID NO:2) to a degree substantially lower than (i.e., less than one-third of, when measured by hybridization to cellular mRNA) that of a normal cell from the same type of tissue as said carcinoma cells; (2) treating the first cell with a compound which increases the concentration of maspin (SEQ ID NO:2) in or around the first cell; and (3) comparing the invasive capacity of each of the first and second cells in an in vitro assay such as that described below, wherein a decrease in invasive capacity of the (treated) first cell relative to that of the (untreated) second cell is an indication that (a) the compound is potentially useful for treatment of carcinomas, and (b) the carcinoma from which the cells are derived is potentially treatable with the compound. This assay is also useful for detecting maspin activity in a biological sample (e.g., during the process of purification of maspin, or for testing the biological activity of maspin fragments or derivatives, or for determining the presence of maspin in a sample of blood, milk, or other biological fluid), wherein a decrease in invasive capacity of the (treated) first cell relative to that of the (untreated) second cell is an indication that maspin, or maspin biological activity, is present in the sample.

Other features and advantages of the invention will be apparent from the following detailed description, and from the claims.

BRIEF DESCRIPTION OF THE DRAWINGS

FIG. 3 is a representation of the complete cDNA sequence (SEQ ID NO: 1) and predicted amino acid sequence of maspin (SEQ ID NO:2). cDNA sequencing was performed using ABI 373A Automated DNA Sequencer at the core facility of Dana-Farber Cancer Institute. The polyadenylation signal is underlined.

FIG. 4 is a comparison of the amino acid sequence of maspin (SEQ ID NO:2) with that of other serpins. Identical residues are boxed. Three regions used for antibody production are underlined. The arrow denotes the proposed reactive center of maspin. At, α1-antitrypsin (SEQ ID NO:3); ei, human monocyte/neutrophil elastase inhibitor (SEQ ID NO:4); ovalbu, ovalbumin (SEQ ID NO:5); pai1, human plasminogen activator inhibitor type 1 (SEQ ID NO:6); pai2, human plasminogen activator type 2 (SEQ ID NO:7); serapin, horse serapin (SEQ ID NO:8).

FIG. 5A is a Western blot analysis of maspin protein from normal and tumor cells. Cells were lysed in SDS-loading buffer, and extracts were electrophoresed on 10% SDS gel and transferred on to Immobilon membrane. Maspin was detected by antiserum AbSiA using the ECL system. Lane 1, 76N; lanes 2–5, tumor cells MCF7, MDA-MB-435, ZR75-1; lane 6, MDA-MB-435 neo transfectant; lane 7, MDA-MB-435 maspin transfectant.

FIG. 5B is a Western blot showing detection of maspin protein in normal cells, using immunoprecipitation. Growing normal cells (70N) were labeled with an $^{35}$S-labeled mixture of methionine and cysteine, and immunoprecipitated with on of four anti-maspin antibodies (lane 1, preimmune serum; lane 2, AbS3A; lane 3, AbS4A; lane 4, AbS1A).

FIGS. 6A–F are photographs of tissue sections stained by immunoperoxidase to illustrate maspin protein expression in acetone-fixed normal mammary epithelial cell cultures (FIG. 6A), and in formalin-fixed paraffin embedded sections of benign (FIG. 6B) and carcinomatous breast tissue (FIG. 6C, ductal carcinoma in situ; FIGS. 6D and 6E, invasive ductal carcinomas; FIG. 6F, pleural effusion containing metastatic breast cancer). Maspin-immunoreactive sites were unmasked in formalin-fixed sections by pretreatment of the sections in 10% sucrose at 80° C. for 2 hours. Both cell cultures and tissue sections were incubated with 5 µg/ml of AbS4A followed by immunoperoxidase detection employing biotinylated tyramine (Adams, J. Histochem. Cytochem 40:1457, 1992). 3-Amino-9-ethylcarbazole was used as the chromagen and nuclei were counterstained with Mayer's hematoxylin. Presorbtion of the primary antibody AbS4A with immunizing peptide eliminated all specific maspin staining. Key: sm, secreted maspin; L, luminal cell; myo, myoepithelial cell; f, fibroblast; dcis, ductal carcinoma in situ; idc, invasive ductal carcinoma; nd, normal benign breast duct; pe, pleural effusion.

FIG. 7 is a Western analysis of maspin in MDA-MB-435 transfectants. Maspin was detected by peptide affinity purified antibody AbS1A. Lanes 1–5, neo transfected; lanes 6–12, maspin transfectant clones T1, T4, T5, T6, T7, T2 and T3, respectively.

DETAILED DESCRIPTION
IDENTIFICATION OF MASPIN

Figure 1:
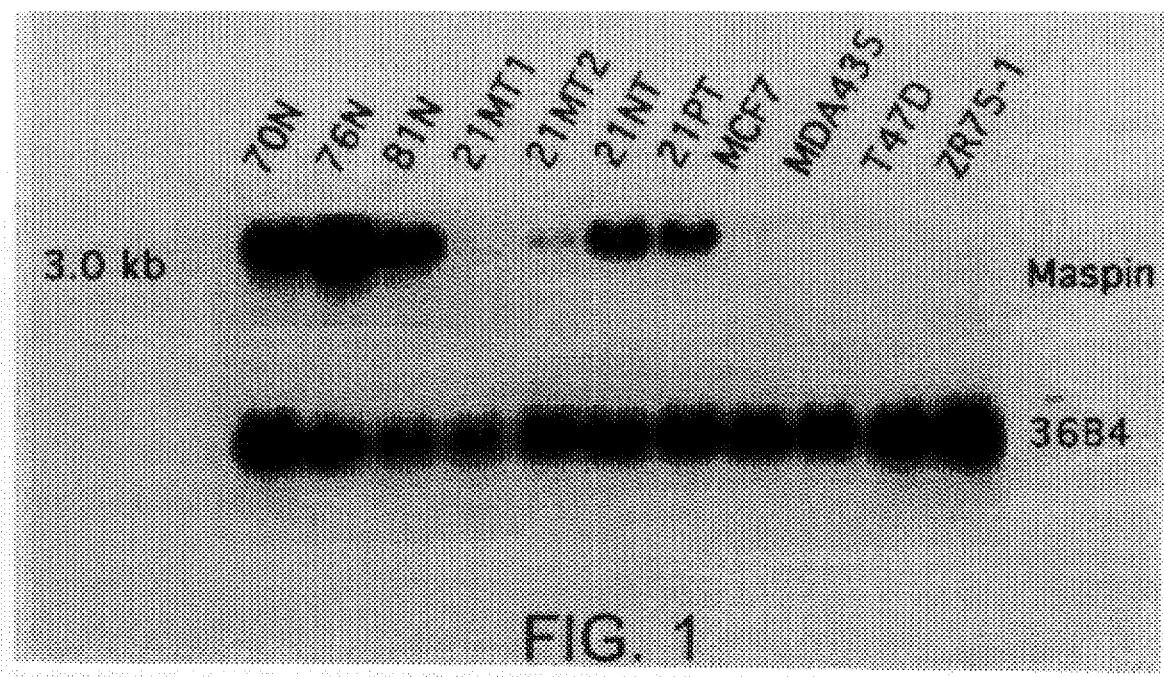
FIG. 1 is a Northern blot analysis of maspin expression in normal and tumor cells. Total cellular RNA was isolated from exponentially growing cells cultured in DFCI-1 medium (Band et al., Proc. Natl. Acad. Sci. USA 86:1249, 1989). 20 ug RNA was electrophoresed on 1% formaldehyde agarous gel, transferred to nylon membrane and hybridized with $^{32}$P-labeled maspin probe. Lanes 1–3, normal breast epithelial cells 70N, 76N, 81N; lanes 4–11, breast tumor cells 21MT1, 21MT2, 21NT, 21PT, MCF7, MDA-MB-435, T47D, and ZR75-1.
Figure 2:
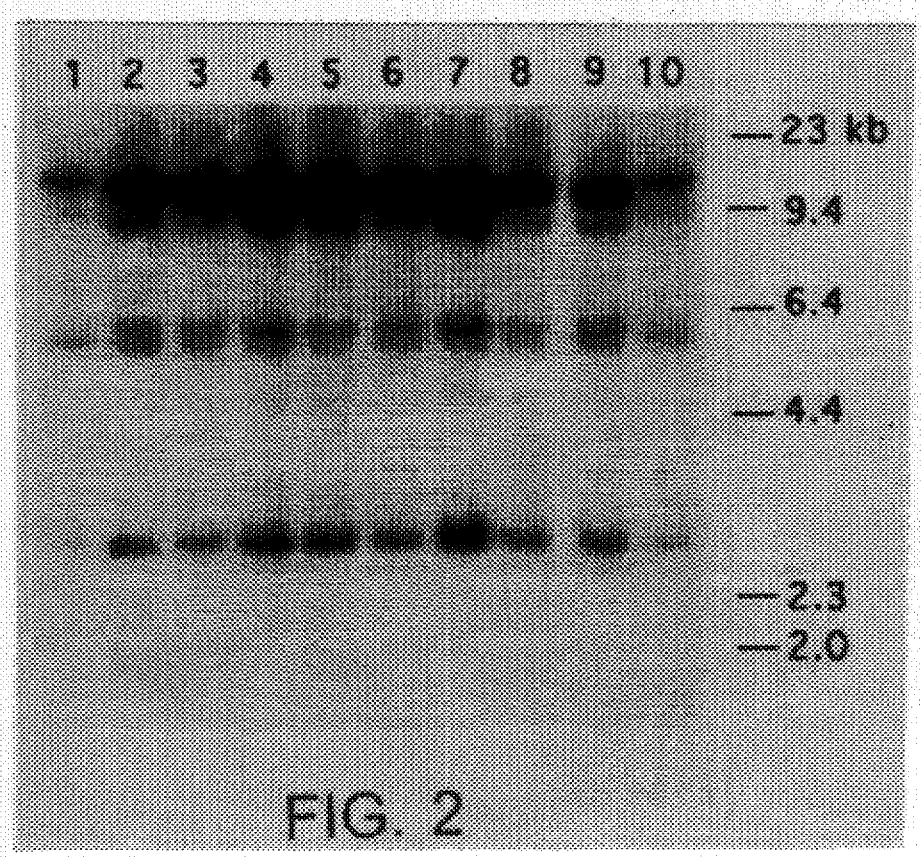
FIG. 2 is a Southern blot analysis of the maspin gene. DNA (20mg) was digested with XbaI, fractionated on 1% agarose gel and transferred to nylon membrane. The blot was hybridized with $^{32}$P-labeled full length maspin cDNA. Lanes 1–2, normal breast cell 70N and 76N; lanes 3–10, breast tumor cell lines 21MT1, 21MT2, 21NT, 21PT MDA-MB-231, MDA-MB-435, MCF7, ZR75-1.

Using subtractive hybridization (as described in U.S. appication Ser. No. 07/844,296), a new member of the serpin family has been isolated, cloned, sequenced, and partially characterized. The gene was named maspin because of its sequence similarity to other serpins, and its initial identification in mammary epithelial cells. As shown in FIG. 1, the maspin gene expresses a single 3.0 kb mRNA in three normal mammary epithelial cell strains (Band et al., Proc. Natl. Acad. Sci. USA 86:1249, 1989) but not in a series of tumor cell lines including those shown in FIG. 1 as well as MDA-MB-157, MDA-MB-231, MDA-MB-436, MDA-MB-468, BT549, and HS578T (not shown). Two cell lines from primary tumors of a single patient (21PT and 21NT) (Band et al., Cancer Res. 50:7351, 1989) expressed maspin mRNA, but at a much reduced level compared with the normal cells. Neither foreskin fibroblasts nor breast-derived fibroblasts expressed detectable maspin mRNA. Southern analysis of DNA from normal and tumor cells (FIG. 2) using the restriction enzyme XbaI, which produced 5 fragments that hybridized with the maspin probe, showed no differences in pattern among them. Thus the gene is present and unaltered at this level of resolution in the tumor cell lines including the 21T series, in which the primaries (21PT, 21NT) express the mRNA and the cells of metastatic origin do not. This evidence suggests that maspin is a Class II candidate tumor suppressor gene, down-regulated but not mutated in cancer cells (Lee et al., Proc. Natl. Acad. Sci. USA 88:2825, 1991; Sager et al., FASEB J. 7:964–970, 1993) Maspin cDNA (SEQ ID NO:1) was isolated from a normal human mammary epithelial cell library (76N), as described in U.S. application Ser. No. 07/844,296. The cDNA sequence contains 2584 nucleotides with a polyadenylation signal located 16 nucleotides from the 3' terminus of the sequence, as shown in FIG. 3. The full length sequence includes 75 nucleotides of the 5' untranslated region and 1381 nucleotides of 3' untranslated region. The initiation codon and surrounding nucleotides fit the Kozak consensus (Kozak, Nucleic Acid Res. 12:857, 1984). The cDNA encodes a protein of 375 amino acids with an N-terminal methionine and C-terminal valine. Maspin also contains 8 cysteine residues, and may utilize two or more disulfide bonds to stabilize its tertiary structure.

Multiple alignment studies based on data base searches using BLAST at the National Center for Biotechnology Information and analyzed by the GCG Pileup program demonstrate close homology to the serpin superfamily of serine proteinase inhibitors (see FIG. 4). Serpins are a diverse family of proteins related by virtue of primary sequence homology spanning the entire length of each molecule, and varying from 15–50% at the amino acid level and higher at the DNA level. Maspin exhibits closest homology at the protein sequence level to the equine (43%) and human neutrophil-monocyte elastase inhibitors (39%), human PAI-2 (31%), human squamous cell carcinoma antigen (SCCA, 34%), and chicken egg albumin (31%).

THE SERPIN FAMILY

Serpin molecules possess important physiological functions, including proteinase inhibition (inhibitors of complement activation, coagulation, kinin formation, and fibrinolysis), hormone transport (thyroxine binding globulin, cortisol binding globulin), vasoactive peptide donors (angiotensinogen), and unknown function (ovalbumin) (for reviews see Travis et al., Biol. Chem Hoppe-Seyler 371:3, 1990; Huber et al., Biochem. 28:1, 1989).

The crystallographic structures have been solved for native and cleaved ovalbumin, cleaved al-antitrypsin, cleaved α1-antichymotrypsin, and latent plasminogen activator inhibitor-1 (Stein et al., Nature 347:90, 1990; Wright et al., J. Mol. Biol. 213:513, 1990; Loebermann et al., J. Mol. Biol. 177:531, 1984; Baumann et al., J. Mol. Biol. 218:595, 1991; Mottonen et al., Nature 355:270, 1992). In each case, the structures have proven to be very similar, indicating a conserved molecular framework. These studies confirm the usefulness of molecular modeling to make predictions concerning the unsolved structures of other serpins.

Active inhibitory serpins (S-form) interact with their target proteases with a 1:1 stoichiometry to form stable, denaturation-resistant complexes, in which the protease is inactive. Of primary importance in determining the specificity of the target protease is the nature of the $P_1$ residue of the reactive center. Serpins with Ala, Val, or Met at the $P_1$ position are inhibitors of elastase-like proteinases, while serpins with Arg at the $P_1$ position inhibit trypsin-like proteases.

The alignment of maspin with other serpins (FIG. 4) provides preliminary evidence that maspin may also function as a proteinase inhibitor. The homology alignment identifies Arg as the putative $P_1$ residue in maspin, suggesting that it may inhibit trypsin-like proteases such as plasmin, uPA, and tPA. Because of the gap preceding the reactive site peptide bond, other alignments are possible, but each likely alignment provides a $P_1$ residue with the potential for generating inhibitory activity.

IDENTIFICATION OF MASPIN PROTEIN USING ANTI-MASPIN ANTIBODIES

Three poorly conserved sequences (underlined in FIG. 4 as S1A, S3A, and S4A) were selected as the basis for designing synthetic oligopeptides for polyclonal antibody production, using conjugation to keyhole limpet hemocyanin [Harlow et al., Antibodies, A Laboratory Manual, Cold Spring Harbor Laboratory, New York, 1988 (Chapter 8)]. The antisera were respectively designated as AbS1A, AbS3A and AbS4A. AbS4A recognizes the reactive center loop encompassing the putative p1–p1' residue. As shown in FIG. 5A, a 42 kDa band was detected on a reducing SDS gel, both in normal cells (70N; lane 1) and in tumor cells (MDA-MB-435) transfected with maspin cDNA (lane 7). This molecular weight is consistent with the estimated size based on the primary sequence. All three antibody preparations reacted with this 42 kDa protein. No protein was detected in breast tumor cell lines MCF7, MDA-MB-468, MDA-MB-435, and ZR75-1, or in MDA-MB-435 transfected with control vector (lanes 2–6). All three antisera precipitated a 42 kDa band from normal cell extracts (FIG. 5B). These results demonstrate that the maspin gene encodes a 42 kDa protein present in normal mammary epithelial cells and absent in tumor cell lines that do not express the mRNA.

MASPIN EXPRESSION IN BENIGN AND MALIGNANT BREAST

Indirect immunofluorescence microscopy of a normal human mammary epithelial cell strain (76N) demonstrated that maspin protein is localized mainly to the pericellular space, with weak staining in the cytoplasm (FIG. 6A). These results demonstrate that maspin is secreted into the ECM, and may interact with its target protease in the ECM and/or on the plasma membrane. Primary mammary tumor cells grown in culture (21PT) exhibited weak staining with a pattern similar to the normal cells, consistent with their low-level expression of maspin mRNA (FIG. 1), whereas MDA-MB-435 cells were negative. Each of the maspin antisera AbS1A, AbS3A, and AbS4A generated similar staining patterns that could be preabsorbed by the corresponding immunizing peptide.

As shown in FIGS. 6A and B, acetone-fixed cryosections and formalin-fixed, paraffin-embedded sections of benign breast tissues (n=6) and benign epithelium adjacent to invasive carcinomas were maspin positive when immunostained with AbS4A. Maspin expression was particularly intense in myoepithelial cells, both within large ducts and terminal duct lobular units (TDLU). Luminal epithelial cells were heterogeneously positive (often showing weak granular cytoplasmic immunopositivity of some cells), with more intense apical reactivity and some positivity of intraluminal secreted material (FIG. 6B). Inflammatory and stromal cells were always negative.

Figure 9:
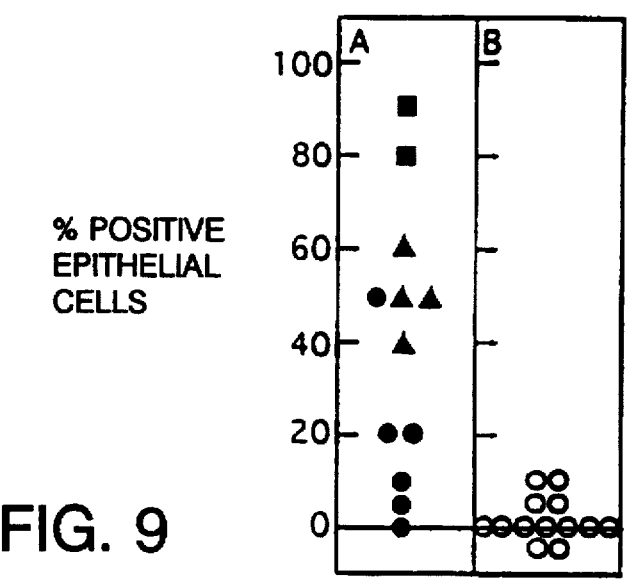
FIG. 9 is a chart illustrating the reactivity of AbS4A antiserum with several mammary carcinoma samples. Affinity-purified AbS4A (at 5 µg/ml) was reacted with formalin-fixed 5 µm paraffin-embedded sections that were pretreated in 10% sucrose at 80° C. for 1 hour. Antibody-antigen complexes were visualized by the modified immunoperoxidase method using biotinylated tyramine (Adams, J. Histochem. Cytochem. 40:1457, 1992). The % positive cells denotes the number of carcinoma cells that were reactive with AbS4A divided by the total number of tumor cells×100 in (A) primary breast carcinomas, and (B) mammary lymph node metastases and pleural effusions (o). Each symbol represents a specimen from a different individual. Many tumor cells in ductal carcinomas in situ (■) expressed maspin. Differentiated components of invasive breast carcinomas (▲) expressed some maspin. Poorly differentiated neoplasms (●) failed to exhibit maspin immunoreactivity.

Twelve invasive carcinomas of the breast, eleven regional lymph node metastases, two pleural effusions containing metastatic breast cancer, and adjacent in situ epithelial elements were also evaluated for maspin expression (FIG. 9). Carcinoma in situ was weakly immunopositive, and apical expression was occasionally noted. Maspin expression was highest within myoepithelial cells (adjacent to the basement membrane). Secreted maspin was sometimes observed in the luminal space of benign breast (FIG. 6B) and ductal carcinomas in situ (FIG. 6C), and rarely in invasive ductal carcinomas, as for example in the well-differentiated tubular variant (FIG. 6D). Most malignant cells in invasive carcinomas failed to express maspin (FIG. 6E), but a minority of cells in well differentiated tumors expressed maspin focally (FIG. 9). Maspin was undetectable or very weakly expressed in all lymph node metastases and pleural effusions examined (FIG. 6F). These findings suggest a biological role for maspin in the benign breast and a potentially pivotal alteration in maspin expression during the progression of breast cancer.

DECREASED GROWTH IN NUDE MICE OF TUMOR TRANSFECTANTS EXPRESSING MASPIN

Tumor cell line MDA-MB-435 forms tumors at the site of orthotopic injection and metastasizes in nude mice (Price et al., Cancer Res. 50:717, 1990). To investigate whether maspin has inhibitory effects on tumor formation in nude mice, MDA-MB-435 cells were transfected with an expression vector encoding maspin under the control of the CMV promoter (Tomasetto et al., J. Cell Biol. 122:157, 1993). The exogenous gene expressed a 3.0 kb mRNA and a 42 kDa protein at levels similar to those seen in normal cells, whereas no maspin was expressed by the neo-controls (FIG. 7). The low levels of maspin in transfected clones T2 and T4 resulted from instability in maspin transfectants. In cell culture, the maspin transfectants, the neo-controls, and the MDA-MB-435 parental cells all grew at the same rate in alpha-MEM medium containing 5% fetal calf serum (data not shown).

Four maspin transfectants and two vector control transfectants were tested in nude mice as described (Price et al., Cancer Res. 50:717, 1990). Table 1 summarizes the results obtained from two duplicate experiments. At 10 weeks post-inoculation, all mice were sacrificed, and their tumors excised and weighed. Between 6 and 10 weeks, some mice died due to tumor burden or illness. These mice are not included in Table 1. Three of the four maspin transfectant clones produced much smaller tumors than the vector control clones, whereas one clone (T1) grew at the same rate as MDA-MB-435 and the neo-controls. Using the Student t-test, the differences between maspin transfectants and neo-controls were significant whether or not T1 was included in the calculations.

These results show unequivocally that maspin expression leads to growth inhibition of injected transfectants compared with controls. It is obvious by inspection that T1 is not inhibited, whereas the other three transfectants are strongly inhibited. The inhibitory effect of maspin on tumor growth is not unexpected, since other laboratories have reported effects of proteases in inducing growth factor expression indirectly, perhaps via cleaved components of the ECM (Testa et al., Cancer Metastasis Rev. 9:353, 1990).

DECREASED INVASIVE CAPACITY OF MASPIN TRANSFECTANTS

Figure 8:
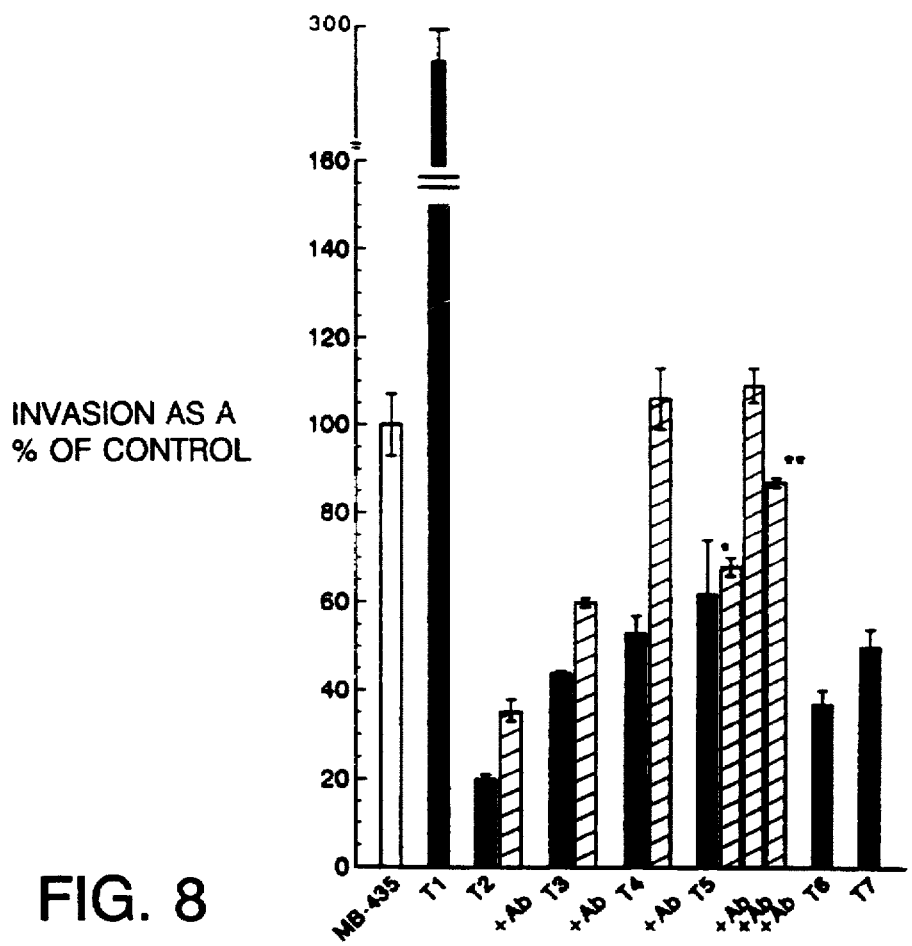
FIG. 8 is a bar graph illustrating the effect of maspin transfection into MDA-MB-435 cells on invasive potential in vitro in the presence or absence of antibodies to maspin. The invasive ability of maspin-transfected clones (T1–T7) to penetrate reconstituted basement membrane-coated (Matrigel; Becton Dickinson, Boston, Mass.) polycarbonate filters (containing 10 mm pores) was measured over 72 h using the Membrane Invasion Culture System (MICS). $1 \times 10^5$ cells were seeded into the upper wells of the MICS chamber onto the Matrigel-coated filter in DMEM medium containing 10% NuSerum (Becton Dickinson). After 72 h incubation at 37° C. with constant $O_2$ and $CO_2$ exchange, the cells that invaded the filter were collected, stained and counted with the aid of a light microscope. The invasion data of the non-transfected MDA-MB-435 cells were normalized to 100%, and the invasion data of the experimental and control transfectants are expressed as a percentage of this control. The data represent the average of two separate experiments; error bars represent the standard error of the mean and are based on n=6 for each experiment. To neutralize the activity of secreted maspin, selected clones were pretreated with AbS4A maspin antibody continuously during the course of the invasion assay at a concentration of 1.0 mg/ml, unless stated otherwise. In selected experiments, additional concentrations of the antibody were tested: *0.1 and **3.0 mg.ml. The invasive potential of the untreated clones was normalized to 100%, and the invasive potential of the treated clones is indicated as a percentage of the untreated respective clones.

An in vitro assay of tumor cell invasion through reconstituted basement membrane matrix (Matrigel) has been used to assess the functional activity of maspin (Hendrix et al., Cancer Letters 38:137, 1987). Seven maspin transfectant clones and 5 neo vector transfectant clones were compared with the parental MDA-MB-435 cells. Six (T2-T7) of the 7 maspin transfectant clones showed reduced invasive ability; as shown in FIG. 8, this difference was neutralized in a dose-dependent manner with the peptide affinity-purified antibody AbS4A. The antibody blocked the inhibitory effect of the recombinant maspin produced by the transfected cells, resulting in elevated invasive activity. Since AbS4A recognizes the reactive center of the protein, it is likely that the site of interaction with the target protease was blocked.

By immunofluorescence microscopy, we noted that maspin expression was heterogeneous in the pre-invasion cells. However, in the post-invasion cells, staining revealed that more than 95% were maspin-negative. Thus, the effectiveness of maspin in inhibiting invasion is somewhat underestimated in these experiments, owing to heterogeneity of expression in the transfectant population. Furthermore, our evidence that only the maspin-negative cells crossed the Matrigel barrier further demonstrates that the cells expressing maspin were inhibited in their ability to invade.

In addition, five neo-control transfectants were tested for their invasive capacity (data not shown). Of these, two expressed invasive activity comparable to the parental cells, whereas three of them showed a decrease in invasive activity. However, none of the five neo-controls responded to the AbS4A antibody, indicating that maspin was not responsible for the decreased invasiveness of the controls. This result is consistent with the absence of maspin protein in the neo-controls, as shown in FIG. 5A. In light of Liotta's three-step invasion model (Liotta et al., Cancer Res. 51:5054, 1991) (i.e., adhesion, degradation, and motility), the adhesive ability of all 12 transfectants (7 containing maspin and 5 controls) to Matrigel matrix were examined; no differences among them were found (data not shown).

These data support the hypothesis that the activity of maspin is associated with the inhibition of tumor cell invasive potential. It is noteworthy that the same transfectant clone (T1) which showed no inhibition of invasive potential in the invasion assay, also showed no decrease of tumor size when tested in the nude mouse assay. This clone, which is more invasive than the parental tumor cells, may overexpress a novel protease, and merits further investigation.

CHROMOSOMAL LOCATION OF MASPIN

A panel of 24 human-rodent somatic cell hybrids was used to map the chromosomal location of the maspin gene. All hybrids retained a single human chromosome except one line that contained both chromosome 20 and a low percent of chromosome 4, and one that contained both chromosomes 1 and X. In human DNA, the maspin probe detected a major 5.4 kb HindIII fragment, which was clearly resolved from a weakly hybridizing Chinese hamster fragment of about 20 kb. The presence of the 5.4 kb human maspin sequence in the hybrid clones correlated only with the presence of human chromosome 18 (Table 2). Only one of the 24 hybrids analyzed was positive for maspin; this hybrid contained chromosome 18 as the sole human DNA. No discordancies for localization to chromosome 18 were found, whereas there were at least two discordancies for localization to any other chromosome. The maspin gene has been localized to 18q21.3, the same chromosomal region as a closely related gene, PLANH2, that encodes plasminogen activator inhibitor-2 (PAI-2) (LeBeau et al., Human Gene Mapping 11, Cytogenet. Cell Genet. 58:739, 1991).

EXAMPLE 1

Recombinant Maspin

Using the information provided above, one of ordinary skill can generate a synthetic DNA probe consisting of a 20-nucleotide segment of the maspin cDNA sequence (SEQ ID NO:1), and use that probe to screen at high stringency a cDNA library from an appropriate epithelial cell line such as MCF7. Alternatively, one could design two appropriate PCR primers, based upon the disclosed cDNA sequence, and generate a maspin cDNA either from the same library, or directly from the mRNA of that cell line. Both of these procedures are standard ones readily carried out by one of ordinary skill in the art. Sequencing of the cDNA so obtained will confirm that it is the maspin cDNA disclosed herein. Multiple copies of the cDNA are readily produced by inserting the cDNA into a recombinant vector, and using that vector to transfect a prokaryotic host such as E. coli. This cDNA, or a fragment thereof, can be used to screen epithelial cell cDNA libraries from species other than human [e.g., mammalian species such as mouse, rat, guinea pig, hamster, rabbit, cow, pig, horse, sheep, monkey, and ape; or nonmammalian animals such as birds or insects (e.g., Drosophila); or microorganisms such as yeast] in order to identify the maspin homologs in such other species. It is likely that the stringency of the hybridization conditions would have to be adjusted to take into account the probable lack of complete sequence identity with the human cDNA.

Once the desired maspin cDNA is in hand, it can be inserted into an expression vector and used in an appropriate expression system to generate recombinant maspin protein. The expression system can be any standard system, including prokaryotic (e.g., E.coli), eukaryotic (e.g., yeast, CHO cells, COS cells, or baculovirus in insect cells), or cell-free. Since the protein appears to be secreted, it can be collected from the culture filtrate of E. coli, or from the medium bathing the transfected insect or other eukaryotic cells. Standard methods of protein purification, optionally including passage over an immunoaffinity column, can be employed to isolate the recombinant protein.

EXAMPLE 2

Diagnostic Assay Utilizing Hybridization Probe

As described above, a nucleic acid probe containing some or all of the maspin-encoding sequence of the invention (SEQ ID NO:1) can be used to detect maspin mRNA in a sample of epithelial cells (e.g., a tissue section) suspected of being cancerous. The probe used would be a single-stranded DNA or RNA (preferably DNA) antisense to the coding sequence shown in FIG. 3. It could be produced by synthetic or recombinant DNA methods, and labelled with a radioactive tracer or other standard detecting means. The probe could include from 15 to the full 1125 nucleotides of coding sequence, and preferably is at least 30 nucleotides long. The assay can be carried out by standard methods of in situ hybridization or Northern analysis, using stringent hybridization conditions. Control hybridization assays can be run in parallel using normal epithelial cells or tissue sections from the same type of tissue as the test sample, and/or cells from a known carcinoma or carcinoma-derived cell line, or a cancer-containing tissue section. Cells which exhibit a substantially decreased level, or absence, of hybridization to the probe, compared to the level seen with normal epithelial cells, are likely to be cancerous. The amount of hybridization can be quantitated by standard methods, such as counting the grains of radioactivity exposed emulsion on an in situ hybridization assay of a biopsy slide, or by densitometric scan of a Northern blot X-ray film. Alternatively, comparison of the test assay results with the results of the control assays can be relative rather than quantitative, particularly where the difference in levels of hybridization is dramatic. This assay is useful for detecting cancerous cells in breast epithelial tissue or in any other type of tissue in which maspin is normally expressed.

EXAMPLE 3

Diagnostic Assay Utilizing Antibody Probe

Antibodies specific for maspin can be generated by standard polyclonal or monoclonal methods, using as immunogen a purified, naturally-occurring maspin; recombinant maspin; or any antigenic fragment of maspin which induces antibodies that react with naturally-occurring maspin. The latter fragment can be produced by synthetic or recombinant methods, or by proteolytic digestion of holo maspin. (Three examples of fragments useful for antibody production are described above.) If desired, the antigenic fragment can be linked by standard methods to a molecule which increases the immunogenicity of the fragment, such as keyhole limpet hemocyanin (as described above). The polyclonal or monoclonal antibodies so produced can be screened using purified recombinant or naturally occurring maspin, or as described above, to select those which form an immunocomplex with maspin specifically.

The antibodies so produced are employed in diagnostic methods for detecting cells, tissues, or biological fluids in which the presence of maspin is decreased relative to normal cells, an indication that the patient has a carcinoma. The sample tested may be a fixed section of a tissue biopsy, a preparation of cells obtained from a suspect tissue, or a sample of biological fluid, such as blood, serum, urine, sweat, tears, cerebrospinal fluid, milk, ductal fluid, or semen. Standard methods of immunoassay may be used, including those described above as well as sandwich ELISA. If the tested cells express no detectable maspin protein in this assay, while normal cells of the same tissue type do express a detectable level of maspin, the tested cells are likely to represent an advanced, metastatic carcinoma. If the tested cells express a decreased but consistently detectable level of maspin, the tested cells are probably from an early stage carcinoma that is not yet metastatic. Where the sample tested is a biological fluid into which maspin would normally be secreted, the fluid may be directly contacted with the anti-maspin antibody, or can be first partially processed (e.g., centrifuged, pre-cleared with other antibodies, dialyzed, or passed over a column) before using the anti-maspin antibody. The amount of immunocomplex formed between the proteins of the sample and the anti-maspin antibody is then determined, and can be compared to a normal control run in parallel, or to a previously-determined standard.

EXAMPLE 4

In Vivo and in Vitro Assays

The in vivo assay described above, in which tumor growth is measured in severely immunodeficient mice (e.g., nude mice), is useful in a number of applications concerning the present invention. For example, the assay can be used to determine (1) whether or not growth of a given carcinoma is inhibited by treatment either with maspin or an agent which increases the concentration of maspin in the carcinoma cells; or (2) whether or not a given candidate compound, which may be known to increase maspin expression in carcinomas in which maspin expression is down-regulated, can in fact inhibit growth of such carcinomas. The nude mice (or any other severely immunodeficient animal, such as a rat, rabbit, or other mammal) can also be adapted to study the effect of a given treatment on the rate of metastasis of the tumor, using standard methods of in vivo analysis of metastasis.

A second type of assay described above, the in vitro assay of tumor cell invasion through reconstituted basement membrane matrix (e.g., MATRIGEL®), is also generally useful with respect to the present invention. Using this assay, the increase in invasive capacity of a given carcinoma over time, or of a series of carcinomas from different patients, can be correlated with the degree of inhibition of maspin expression in each carcinoma sample. The assay can be used to screen various treatment protocols to determine whether a given maspin-increasing protocol is effective in reducing invasive capacity in a given carcinoma.

EXAMPLE 5

Assay for Presence of Intact Gene

If expression of the maspin tumor suppressor gene is down-regulated in the cells of a given carcinoma, but the gene remains present and intact in such cells, it is possible that the cells could be treated in a way that stimulates re-expression of the gene and thereby reverses or at least halts the progression of the carcinoma. This strategy would require affirmation that the gene remains intact and therefore available for up-regulation in the particular cancer cells to be treated. A Southern analysis of genomic DNA from the cancer cells and normal cells, such as described above, would provide evidence that the maspin gene in the cancer cells is largely intact. Use of a battery of restriction enzymes would permit a more rigorous analysis of whether changes in the gene sequence had occurred in the cancer cells. One could use as hybridization probe full-length maspin cDNA (SEQ ID NO:1), maspin genomic DNA, or a fragment of either. To obtain maspin genomic DNA, a human genomic DNA library is probed with maspin cDNA (SEQ ID NO:1), using standard techniques such as described in Sambrook et al., Molecular Cloning: A Laboratory Manual (2nd Edition), Cold Spring Harbor Laboratory, Cold Spring Harbor, N.Y. (1989), herein incorporated by reference. The expression control elements of the naturally-occurring maspin gene (e.g., promoters and enhancers usually located 5' to the transcription start site, or within one or more introns, but also possibly in the 3' untranslated region) are of particular interest, since down-regulation of transcription is associated with tumor progression.

EXAMPLE 6

Screen for and use of Therapeutic Agents

Carcinoma or other cells in which the endogenous maspin gene is present but down-regulated can be used as a screening tool to identify compounds or treatment strategies which induce re-expression of the maspin gene. Re-expression of other down-regulated candidate tumor suppressor genes has been described: connexin 26, encoding a gap junction protein, by PMA (Lee et al., J. Cell Biol. 118:1213, 1992), and a small calcium binding protein, CaN19, by deoxyazacytidine (Lee et al., Proc. Natl. Acad. Sci. USA 89:2504, 1992). Of particular use in such a screen would be cell lines derived from an appropriate carcinoma, with a control being the same cells transfected with a vector encoding maspin cDNA linked to expression control elements which permit constitutive expression of the cDNA (e.g., the CMV promoter), as described above. However, other cell types with intact but unexpressed maspin genes would also be potentially useful in this screening assay. The cells would be treated in vitro with the candidate compounds, and the amount of maspin expression determined using either a hybridization assay (e.g., Northern analysis) or an immunoassay. The latter could be designed to detect intracellular maspin or secreted maspin, or both. If a given compound is found to stimulate maspin expression in the carcinoma cells, it could then be further tested to see whether treatment with the compound prevents carcinoma growth in the nude mouse model described above. A compound effective both in stimulating maspin expression and in preventing carcinoma growth is a potential therapeutic useful for the treatment of carcinomas down-regulated in maspin expression. Further evaluation of the clinical usefulness of such a compound would follow standard methods of evaluating toxicity and clinical effectiveness of anticancer agents.

EXAMPLE 7

Treatment with Maspin

As discussed above, increasing the amount of maspin in a carcinoma cell appears to correlate with a decrease in both growth rate and invasive activity of the tumor. Thus, it is expected that treating a patient with maspin, or a biologically active (i.e., protease-inhibiting) fragment of maspin, will help counter the effects of down-regulation of the maspin gene in the patient's carcinoma cells. Since maspin is a secreted protein, it is likely that it exerts its tumor growth-suppressing effect extracellularly. A useful treatment protocol will therefore be a simple method such as intravenous injection of the protein in a pharmaceutically acceptable solution in a dosage of 0.001 to 100 mg/kg/day, with the most beneficial range to be determined using routine pharmacological methods. This protocol has the advantage of potentially reaching all metastases of the tumor. Alternative routes of delivery would also be acceptable, such as intramuscular or subcutaneous injection, injection directly into the tumor site, or implantation of a device containing a slow-release formulation. If it is desired to ensure that the exogenous maspin protein is incorporated into the carcinoma cells themselves, the protein could be incorporated into liposomes or another form of carrier which permits substantial amounts of the protein to pass through the cell membrane. Liposomes would also help protect the protein from proteolytic degradation while in the bloodstream.

EXAMPLE 8

Genetic Therapy

As disclosed above, an expression vector encoding maspin can be introduced into carcinoma cells, thereby increasing the production of maspin in the transfected cells, and decreasing the in vivo growth rate of tumors derived from these cells. The transfected cells are also shown above to have a decreased invasive character, compared to untransfected controls. This evidence indicates that the maspin DNA of the invention will be useful for genetic therapy to help control carcinomas characterized by down-regulated maspin expression, or to ensure that early-stage carcinomas which have not yet lost the ability to manufacture maspin do not progress through the progressively down-regulated stages. Standard methods of gene therapy may be employed: e.g., as described in Friedmann, *Therapy for Genetic Disease*, T. Friedman (ed.), Oxford Univ. Press, 1991, pp.105–121. Virus or plasmids containing a copy of the maspin cDNA linked to expression control sequences which permit expression in the carcinoma cell would be introduced into the patient, either locally at the site of the tumor or systemically (in order to reach any tumor cells that may have metastasized to other sites). If the transfected DNA encoding maspin is not stably incorporated into the genome of each of the targeted carcinoma cells, the treatment may have to be repeated periodically.

TABLE 1

Tumor growth of maspin transfected MDA-MB-435 cells. Cells were resuspended in PBS, $5 \times 10^5$ cells were injected into mammary fat pad of nude mice (8–10 weeks old for the first experiment, 4–6 weeks old for the second experiment). Each mouse was injected at two sites. Tumor development was monitored weekly. Numbers in parentheses are the numbers of tumors at 10 weeks.

| Cells | Tumor/Site (6 weeks) | Mean Weight (gram) (10 weeks) |
|---|---|---|
| pCMVneo N1 | 8/10 | 0.74 (7) |
| pCMVneo N2 | 10/10 | 1.77 (6) |
| pCMVmaspin T1 | 8/10 | 1.67 (4) |
| pCMVmaspin T4 | 6/10 | 0.31 (7) |
| pCMVmaspin T5 | 5/10 | 0.35 (7) |
| pCMVmaspin T6 | 8/10 | 0.43 (9) | p = 0.034 (T1–T6)
p = 0.00057 (T4–T6)

TABLE 2

Correlation of maspin sequences with human chromosomes in human-rodent cell hybrids. High molecular weight chromosomal DNAs isolated from parental and hybrid cell lines (obtained from NIGMS as mapping panel 2) were treated with HindIII HundIII, fractionated in 0.8% agarose gels, and transferred to nylon filters. A $^{32}$P-labeled maspin cDNA probe was prepared by oligonucleotide labeling and hybridized in the filters as described (Hagiwara et al., Mol. Cell Biol. 11:2125, 1991).

| Chromosome | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
|---|---|---|---|---|---|---|---|---|---|---|---|---|---|---|---|---|---|---|---|---|---|---|---|---|
| Discordancy Ratio | 2/24 | 2/24 | 2/24 | 2/24 | 2/24 | 2/24 | 2/24 | 2/24 | 2/24 | 2/24 | 2/24 | 2/24 | 2/24 | 2/24 | 2/24 | 2/24 | 0/24 | 2/24 | 2/24 | 2/24 | 2/24 | 2/24 | 3/24 | 2/24 |

What is claimed is:

1. A diagnostic method comprising
providing a test cell from a given type of epithelial tissue, said test cell being suspected of being cancerous;
contacting proteins of the test cell with an antibody which forms an immunocomplex with maspin, having the amino acid sequence of SEQ ID NO:2; and
comparing (1) the amount of immunocomplex formation by said antibody and said proteins, with (2) the amount of immunocomplex formation by said antibody and the proteins of a normal control cell from said type of epithelial tissue, wherein an amount of immunocomplex formation with the proteins of said test cell substantially less than the amount obtained with the proteins of said normal control cell is an indication that said test cell is cancerous.

2. The method of claim 1, wherein said epithelial tissue is mammary epithelial tissue.

3. A method for determining whether a test carcinoma cell represents an (a) early-stage or (b) advanced, metastatic carcinoma, said carcinoma being derived from a type of epithelial tissue in normal cells of which maspin, having the amino acid sequence of SEQ ID NO:2, is detectably expressed, which method comprises the steps of
contacting the proteins of the test carcinoma cell with an antibody which forms an immunocomplex with maspin; and
determining the amount of immunocomplex formed by said antibody and said proteins, wherein the absence of consistently detectable immunocomplex is an indication that said test cell is from an advanced, metastatic tumor.

4. The method of claim 3, wherein an amount of immunocomplex that is consistently detectable but less than that measured in a normal cell of said type of tissue is an indication that said carcinoma is an early stage carcinoma.

5. A method for determining the level of maspin, having the amino acid sequence of SEQ ID NO:2, in a biological fluid, comprising the steps of
obtaining a sample of a biological fluid from an individual;
contacting proteins in said sample with an antibody which forms an immunocomplex with maspin; and
determining the amount of immunocomplex formation by said antibody, said amount being indicative of the level of maspin in said sample.

6. The method of claim 5, wherein said biological fluid is blood, serum, urine, saliva, milk, ductal fluid, tears, or semen.

7. The method of claim 5, wherein said amount is compared to the amount of immunocomplex formation by said antibody in a sample previously or subsequently obtained from said individual.

8. The method of claim 1, wherein said antibody is polyclonal.

9. The method of claim 8, wherein said epithelial tissue is mammary epithelial tissue.

10. The method of claim 1, wherein said antibody is monoclonal.

11. The method of claim 10, wherein said epithelial tissue is mammary epithelial tissue.

12. The method of claim 1, wherein said antibody is specific for an epitope within an amino acid sequence selected from the group consisting of YAKELETVDFKDKLE (SEQ ID NO: 9), GKWMKKFPESETKE (SEQ ID NO: 10), and IEVPGARILQHKDEL (SEQ ID NO: 11).

13. The method of claim 12, wherein said epithelial tissue is mammary epithelial tissue.

14. The method of claim 3, wherein said antibody is polyclonal.

15. The method of claim 3, wherein said antibody is monoclonal.

16. The method of claim 15, wherein an amount of immunocomplex that is consistently detectable but less than that measured in a normal cell of said type of tissue is an indication that said carcinoma is an early stage carcinoma.

17. The method of claim 3, wherein said antibody is specific for an epitope within an amino acid sequence selected from the group consisting of YAKELETVDFKDKLE (SEQ ID NO: 9), GKWMKKFPESETKE (SEQ ID NO: 10), and IEVPGARILQHKDEL (SEQ ID NO: 11).

18. The method of claim 17, wherein an amount of immunocomplex that is consistently detectable but less than that measured in a normal cell of said type of tissue is an indication that said carcinoma is an early stage carcinoma.

19. The method of claim 3, wherein said antibody is polyclonal.

20. The method of claim 19, wherein said biological fluid is blood, serum, urine, saliva, milk, ductal fluid, tears, or semen.

21. The method of claim 19, wherein said amount is compared to the amount of immunocomplex formation by said antibody in a sample previously or subsequently obtained from said individual.

22. The method of claim 5, wherein said antibody is monoclonal.

23. The method of claim 22, wherein said biological fluid is blood, serum, urine, saliva, milk, ductal fluid, tears, or semen.

24. The method of claim 22, wherein said amount is compared to the amount of immunocomplex formation by said antibody in a sample previously of subsequently obtained from said individual.

25. The method of claim 5, wherein said antibody is specific for an epitope within an amino acid sequence selected from the group consisting of YAKELETVD-FKDKLE (SEQ ID NO: 9), GKWMKKFPESETKE (SEQ ID NO: 10), and IEVPGARILQHKDEL (SEQ ID NO: 11).

26. The method of claim 25, wherein said biological fluid is blood, serum, urine, saliva, milk, ductal fluid, tears, or semen.

27. The method of claim 25, wherein said amount is compared to the amount of immunocomplex formation by said antibody in a sample previously or subsequently obtained from said individual.

* * * * *